United States Patent
Yilmaz et al.

(10) Patent No.: US 11,769,391 B2
(45) Date of Patent: Sep. 26, 2023

(54) IN-CABIN TEMPERATURE MONITORING FOR CHILD PRESENCE DETECTION APPLICATIONS

(71) Applicant: Veoneer US, LLC, Southfield, MI (US)

(72) Inventors: Mehmet Fatih Yilmaz, Plymouth, MI (US); Thomas Herbert, Ogden, UT (US)

(73) Assignee: VEONEER US LLC, Wilmington, DE (US)

( * ) Notice: Subject to any disclaimer, the term of this patent is extended or adjusted under 35 U.S.C. 154(b) by 0 days.

(21) Appl. No.: 17/555,571

(22) Filed: Dec. 20, 2021

(65) Prior Publication Data

US 2023/0196899 A1 Jun. 22, 2023

(51) Int. Cl.
| | |
|---|---|
| *G08B 21/22* | (2006.01) |
| *E05F 15/73* | (2015.01) |
| *A61B 5/0205* | (2006.01) |
| *A61B 5/08* | (2006.01) |
| *A61B 5/00* | (2006.01) |
| *B60H 1/00* | (2006.01) |
| *G01S 13/04* | (2006.01) |
| *G01S 13/88* | (2006.01) |
| *G08B 21/18* | (2006.01) |
| *G08B 25/00* | (2006.01) |

(52) U.S. Cl.
CPC ............ *G08B 21/22* (2013.01); *A61B 5/0205* (2013.01); *A61B 5/0816* (2013.01); *A61B 5/6893* (2013.01); *B60H 1/00742* (2013.01); *B60H 1/00964* (2013.01); *E05F 15/73* (2015.01); *G01S 13/04* (2013.01); *G01S 13/886* (2013.01); *G08B 21/182* (2013.01); *G08B 25/008* (2013.01)

(58) Field of Classification Search
CPC .... G08B 21/22; G08B 21/182; G08B 25/008; E05F 15/73; A61B 5/0205; A61B 5/0816; A61B 5/6893; B60H 1/00742; B60H 1/00964; G01S 13/04; G01S 13/886
USPC ....................................................... 340/573.1
See application file for complete search history.

(56) References Cited

U.S. PATENT DOCUMENTS

| | | | |
|---|---|---|---|
| 9,937,830 B1* | 4/2018 | Curry, V ................. | B60N 2/879 |
| 10,195,988 B1* | 2/2019 | Garza ....................... | B60Q 9/00 |
| 10,737,616 B1* | 8/2020 | Kreager ................... | B60N 2/28 |
| 2005/0038582 A1* | 2/2005 | Arndt ...................... | G08B 21/12 |
| | | | 701/31.4 |
| 2009/0204297 A1* | 8/2009 | Friedman ........... | B60H 1/00742 |
| | | | 701/46 |

(Continued)

FOREIGN PATENT DOCUMENTS

EP 3736786 11/2020

*Primary Examiner* — Zhen Y Wu

(57) ABSTRACT

An apparatus comprising a radar component and a temperature sensor. The radar component may be configured to detect a presence of a person in a vehicle and determine an age range of the person detected. The temperature sensor may be configured to determine an ambient temperature in the vehicle and operate independently from a heating and cooling system of the vehicle. The apparatus may be configured to operate when the vehicle is turned off. A processor may be configured to determine an urgency level in response to the age range of the person detected and the ambient temperature. The processor may be configured to generate escalating actions in response to the urgency level.

20 Claims, 9 Drawing Sheets

(56) References Cited

U.S. PATENT DOCUMENTS

| | | | | |
|---|---|---|---|---|
| 2010/0078978 | A1* | 4/2010 | Owens | G08B 21/22 |
| | | | | 297/250.1 |
| 2015/0332578 | A1* | 11/2015 | Borgne | B60N 2/26 |
| | | | | 340/667 |
| 2016/0249191 | A1* | 8/2016 | Avrahami | H04W 4/12 |
| 2017/0129399 | A1* | 5/2017 | Appukutty | B60N 2/289 |
| 2017/0158186 | A1* | 6/2017 | Soifer | B60H 1/00742 |
| 2018/0130327 | A1* | 5/2018 | Rogers | G08B 25/005 |
| 2018/0370431 | A1* | 12/2018 | Wincek | B60Q 1/544 |
| 2019/0077217 | A1* | 3/2019 | Yu | B60H 1/0073 |
| 2019/0232818 | A1* | 8/2019 | Gangu | B60N 2/002 |
| 2020/0058210 | A1* | 2/2020 | Williams | G07C 5/08 |
| 2021/0008959 | A1* | 1/2021 | Lee | B60H 1/00978 |
| 2021/0209927 | A1 | 7/2021 | Hedges et al. | |
| 2021/0225152 | A1* | 7/2021 | Taylor | G08B 21/22 |
| 2021/0253063 | A1* | 8/2021 | Pupillo | B60R 25/31 |
| 2021/0362673 | A1 | 11/2021 | Jeon et al. | |
| 2021/0383670 | A1* | 12/2021 | Rence | G07C 9/00309 |
| 2021/0402846 | A1* | 12/2021 | Yu | B60H 1/00735 |

* cited by examiner

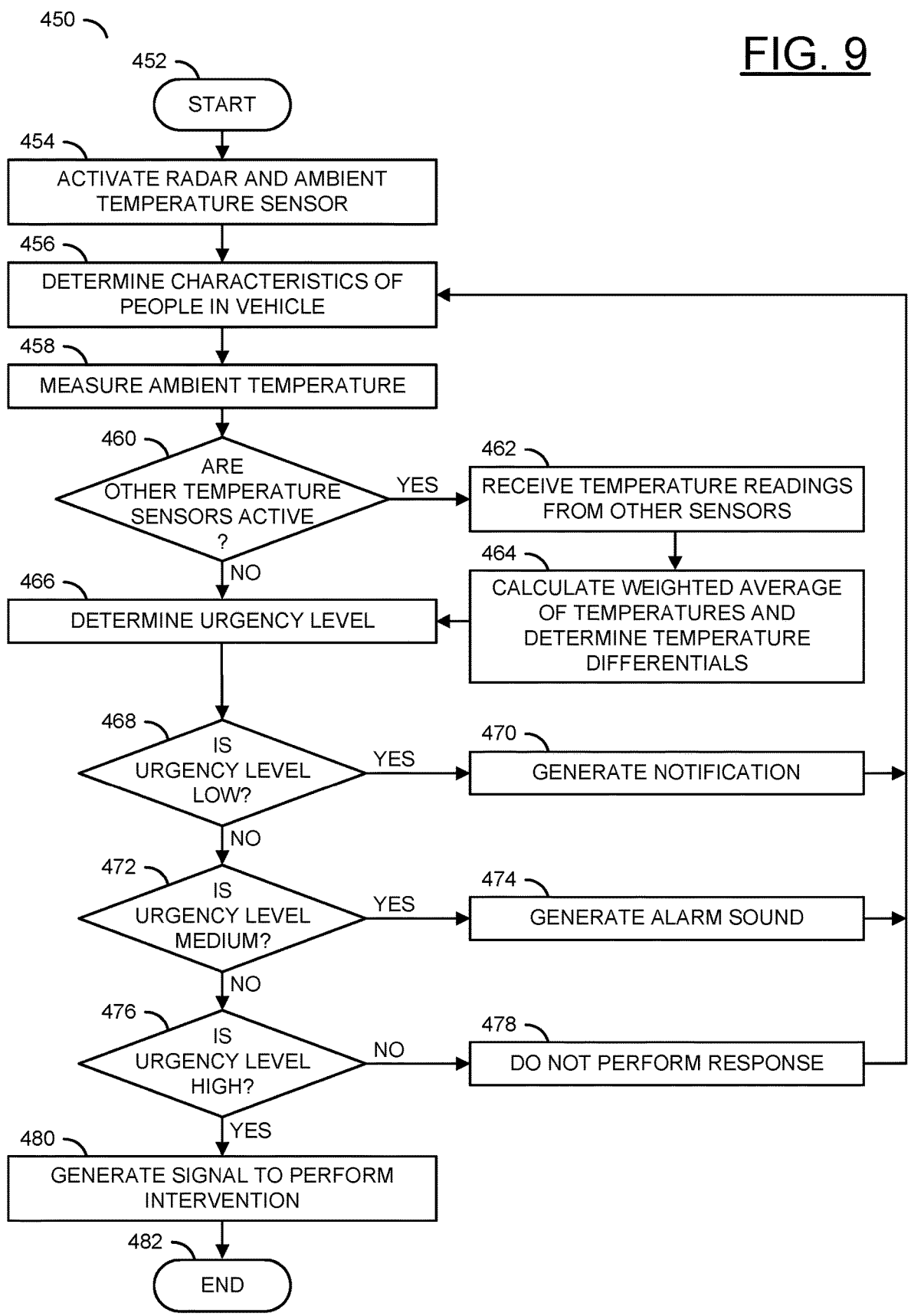

IN-CABIN TEMPERATURE MONITORING FOR CHILD PRESENCE DETECTION APPLICATIONS

FIELD OF THE INVENTION

The invention relates to vehicle sensors generally and, more particularly, to a method and/or apparatus for implementing in-cabin temperature monitoring for child presence detection applications.

BACKGROUND

Regulations for vehicles are starting to require child presence detection for all upcoming vehicles. European regulations for presence detection in vehicles are aligning with the US (i.e., the "Hot Car Act"). Various regulations propose that vehicles be capable of providing alerts in scenarios when children are left in vehicles (as well as other occupants, such as the elderly, adults, pets, etc.).

Conventional detection solutions are capable of detecting the presence of people in vehicles. While the regulations propose a noble goal, overly broad alerts can become a nuisance. Vehicle owners that become annoyed with excessive alerts often search for workarounds to disable the alerts. If a vehicle owner disables all alerts to prevent annoyances, then alerts will not be available in real emergency scenarios. Since not all scenarios where people are left in a parked vehicle are lethal, alerts should be limited to prevent excessive alerts. Danger from being left in a locked vehicle is often a result of temperature and air conditions as well as the duration of stay within the closed vehicle.

It would be desirable to implement in-cabin temperature monitoring for child presence detection applications.

SUMMARY

The invention concerns an apparatus comprising a radar component and a temperature sensor. The radar component may be configured to detect a presence of a person in a vehicle and determine an age range of the person detected. The temperature sensor may be configured to determine an ambient temperature in the vehicle and operate independently from a heating and cooling system of the vehicle. The apparatus may be configured to operate when the vehicle is turned off. A processor may be configured to determine an urgency level in response to the age range of the person detected and the ambient temperature. The processor may be configured to generate escalating actions in response to the urgency level.

BRIEF DESCRIPTION OF THE FIGURES

Embodiments of the invention will be apparent from the following detailed description and the appended claims and drawings.

FIG. 9 is a flow diagram illustrating a method for generating escalating actions in response to an urgency level.

DETAILED DESCRIPTION OF THE EMBODIMENTS

Figure 1:
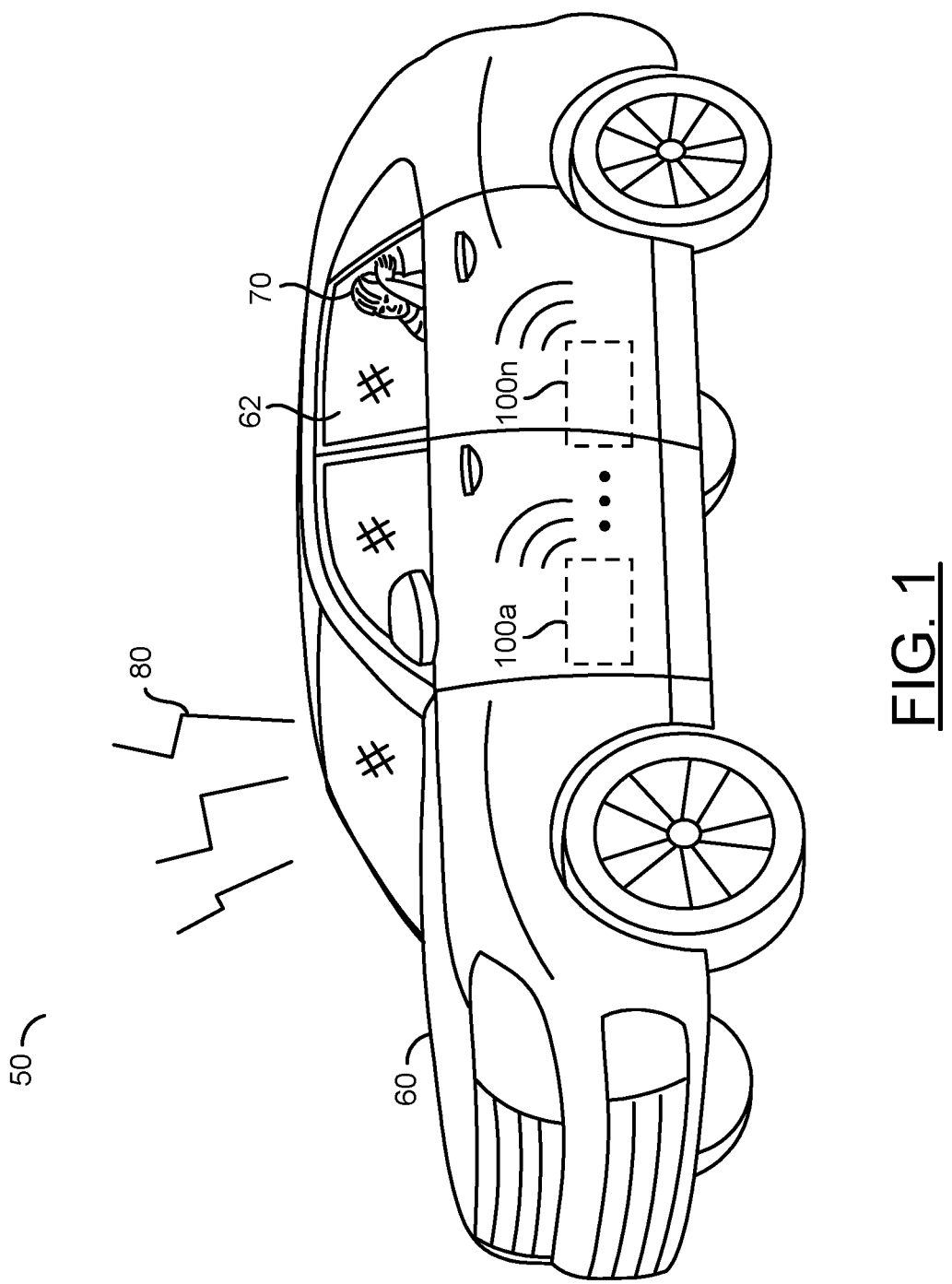
FIG. 1 is a diagram illustrating a vehicle providing an alert with a child left inside.

Embodiments of the present invention include providing in-cabin temperature monitoring for child presence detection applications that may (i) detect a presence of a person in a vehicle while the vehicle is powered off, (ii) measure an ambient temperature in a vehicle, (iii) provide a temperature sensor independent from a vehicle heating and cooling system, (iv) operate efficiently to limit power consumption, (v) determine an urgency level based on presence detection, exposure time and temperature, (vi) perform escalating responses based on changing circumstances, (vii) activate vehicle features to counteract temperature in the vehicle, (viii) prevent alarms from being generated excessively and/or (ix) be implemented as one or more integrated circuits.

Embodiments of the present invention may be configured to implement in cabin monitoring systems (ICMS). The ICMS may be configured to operate while a vehicle is turned off to monitor for the presence of occupants that may be left inside the vehicle. The ICMS may be configured to control the generation of alerts and/or other responses based on conditions that may be detrimental for the detected occupants. In one example, the ICMS may be configured to provide enhancements to EP and US regulations regarding people (e.g., children) being left in locked vehicles.

Embodiments of the present invention may be configured to implement a radar device and/or temperature sensors in the vehicle. The radar device may be configured to detect the presence and/or characteristics of any living beings (e.g., children, adults, the elderly, animals, etc.). Instead of relying solely on presence detection, the temperature sensors may be implemented to monitor for critical temperatures and/or duration of temperatures. The combination of the radar device and the temperature sensors may be configured to detect exposure of vehicle occupants to extreme temperature conditions.

The temperature sensors implemented may operate independent from other temperature sensors in the vehicle. For example, many vehicles implement temperature sensors for heating and cooling (HVAC) systems. The temperature sensor implemented by embodiments of the present invention may be configured to operate independent from HVAC temperature sensors to enable monitoring of ambient temperature changes even while the HVAC system is not operational. By decoupling the temperature measurement from high power consumption devices, such as the vehicle HVAC system, embodiments of the present invention may be configured to operate with efficient power requirements. In an example, as modern vehicles shift to electric and hybrid vehicles, reducing the amount of power consuming devices and/or reducing the amount of time that power consuming devices are active may become more important. The present invention may provide temperature monitoring while the HVAC is not consuming power.

Embodiments of the present invention may be configured to leverage radar hardware with a self-diagnostic temperature sensor. While the vehicle is powered off, the temperature in the vehicle may be continually monitored over an extended period of time. In one example, the radar and/or temperature sensors may remain active after the vehicle is shut off (e.g., approximately 30 minutes after the vehicle is powered down). In response to people detected and the temperature measured, warnings may be generated with escalating severity. In one example, a warning may be generated when an occupant (e.g., a child) is detected in the vehicle. In another example, an alert/alarm may be generated in response to an increase (or decrease) in temperature detected (e.g., in response to the ambient temperature increasing or decreasing by a predetermined number of degrees within a particular amount of time, an escalation of the warning may result). In yet another example, an intervention may be performed in response to the temperature being detected above (or below) a predetermined temperature threshold (e.g., windows may be rolled down, the heating/cooling system may be activated, the doors may be unlocked, etc.).

Embodiments of the present invention may be configured to monitor the cabin temperature independently from the vehicle temperature sensors and signal a potentially dangerous condition (e.g., defined by excessively high or low temperature and/or exposure time). The temperature may be measured by an independent temperature sensor in the radar module. The independent ambient temperature sensor may provide more accurate measurements compared to HVAC temperature sensors (e.g., HVAC temperature sensors rely on the flow of air in the air vents, which may not occur when the vehicle is parked). The independent temperature sensor may provide reliable results. In some embodiments, other temperature information provided by other vehicle components that implement temperature sensors may be received. A weighted average may be calculated in order to account for any temperature differentials within the vehicle.

Referring to FIG. 1, a diagram illustrating a vehicle providing an alert with a child left inside is shown. A scenario 50 is shown illustrating an example context for the present invention. A vehicle 60 is shown in the scenario 50. The vehicle 60 may be turned off (e.g., parked and powered off). In one example, the vehicle 60 may be an electric vehicle (EV). In another example, the vehicle 60 may be a hybrid-electric vehicle. In yet another example, the vehicle 60 may be an internal combustion engine (ICE) vehicle. The type of the vehicle 60 may be varied according to the design criteria of a particular implementation.

An interior 62 of the vehicle 60 is shown. The interior 62 of the vehicle 60 is shown enclosed (e.g., doors are closed and windows are shut). A person 70 is shown within the interior 62. In the example shown, the person 70 may be a child. The person 70 is shown alone within the vehicle 60. The scenario 50 may provide an example of the child 70 left unattended in a parked vehicle (e.g., no adults or other people present in the interior 62).

Multiple lines 80 are shown extending from the vehicle 60. The lines 80 may represent an alert (e.g., an audio alert). The alert 80 may be generated in response to the detection of the child 70 left unattended in the vehicle 60. Generally, the alert 80 may be generated in accordance with regulations that may apply for children being left in vehicles.

Blocks (or circuits) 100a-100n are shown. The circuits 100a-100n may implement radar units. The radar units 100a-100n may be configured to detect the presence of people within the interior 62 of the vehicle 60. The number of radar units 100a-100n implemented by the vehicle 60 may depend on the size of the vehicle 60 and/or potential obstacles within the interior 62. The number of the radar units 100a-100n implemented may be varied according to the design criteria of a particular implementation.

One or more of the radar units 100a-100n may detect the person 70. The radar units 100a-100n may be configured to detect the presence of people in the interior 62 of the vehicle 60 to enable the generation of the alert 80. In some embodiments, the radar units 100a-100n may be configured to detect the person 70 and generate the alert 80 in response to detecting the person 70. In some embodiments, the radar units 100a-100n may be configured to detect the person 70 and provide data about the detection to another component of the vehicle 60 (e.g., an electronic control unit (ECU)) that may generate the alert 80. The combination(s) of components that the radar units 100a-100n may communicate with to enable the generation of the alert 80 may be varied according to the design criteria of a particular implementation.

The radar units 100a-100n may be configured to enable granular control of the generation of the alert 80. For example, the radar units 100a-100n may be configured to suppress the alert 80 unless predetermined criteria are met. In one example, the radar units 100a-100n may prevent and/or disable the alert 80 in response to detection of the person 70 alone. The radar units 100a-100n may be configured to analyze multiple sources of data to ensure the alert 80 is generated in response to scenarios where human intervention and/or attention may be suitable (e.g., potentially dangerous scenarios) without enabling the alert 80 in scenarios that may not need urgent human intervention and/or attention (e.g., may not be dangerous). By analyzing multiple sources of data (e.g., more than presence detection alone), the radar units 100a-100n may be configured to prevent the alert 80 from becoming a nuisance for vehicle owners.

Figure 2:
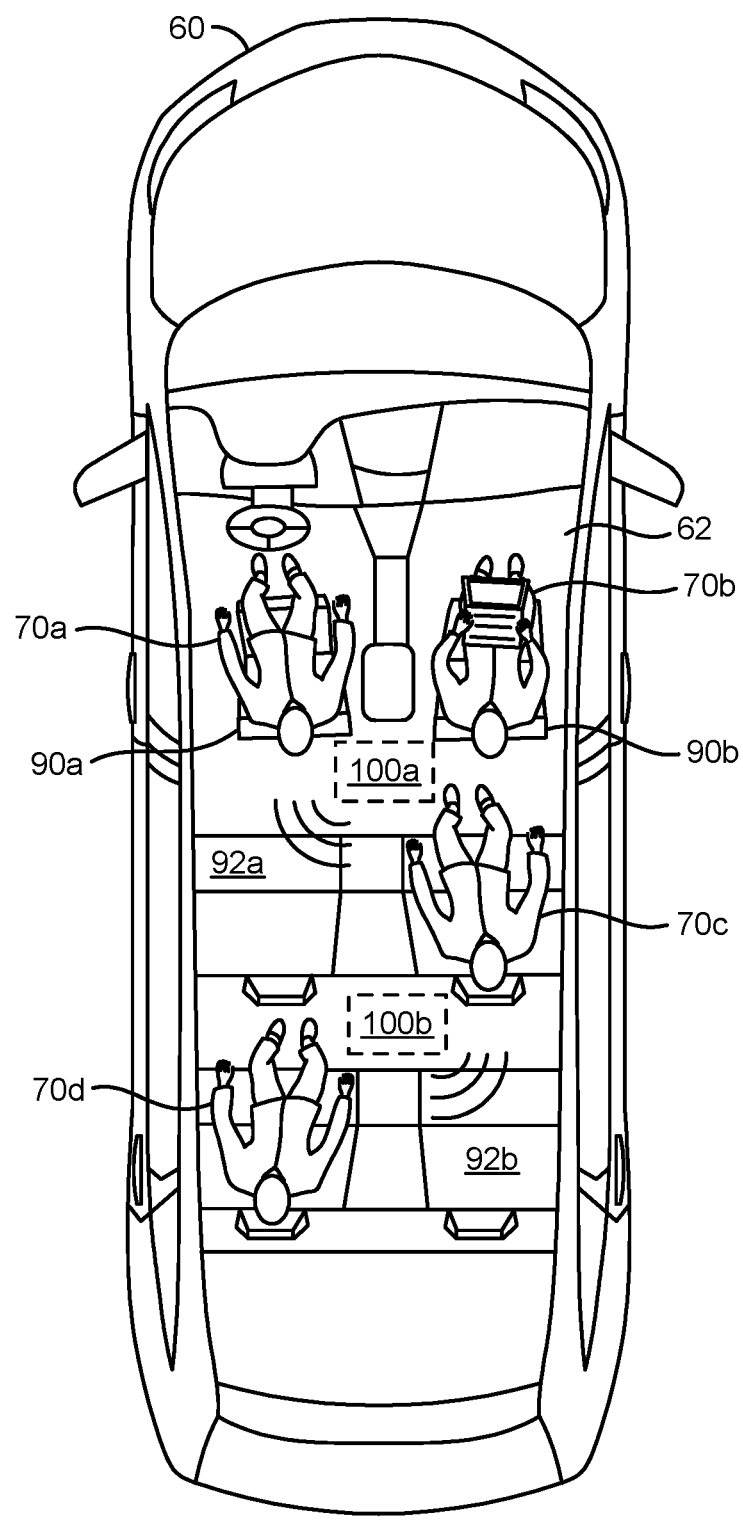
FIG. 2 is a diagram illustrating radar units implemented to detect the presence of people in a vehicle interior.

Referring to FIG. 2, a diagram illustrating radar units implemented to detect the presence of people in a vehicle interior is shown. A top down view of the vehicle 60 is shown. The top down view of the vehicle 60 is illustrated with a top of the vehicle 60 shown as a cutaway to provide a view of the interior 62.

People 70a-70d are shown within the interior 62 of the vehicle 60. The people 70a-70d may represent passengers and/or a driver of the vehicle 60. In the example shown, the people 70a-70d are illustrated as adults. However, the one or more of the people 70a-70d in the vehicle 60 may be any combination of children, teenagers, infants, adults, the elderly, differently-abled people, incapacitated people, etc. In an example, the child 70 shown in association with FIG. 1 may be one of the people 70a-70d. The number and/or characteristics of the people 70a-70d may be varied according to the design criteria of a particular implementation.

Seats 90a-90b are shown in the interior 62. The person 70a is shown in the seat 90a (e.g., a driver in the driver seat 90a). The person 70b is shown in the seat 90b (e.g., a passenger in the front passenger seat 90b). The seats 90a-90b may be a front row of seats of the vehicle 60.

Seat rows 92a-92b are shown. The seat row 92a may be a middle seat row. The person 70c is shown sitting in the middle seat row 92a. The seat row 92b may be a rear seat row. The person 70d is shown sitting in the rear seat row 92b. In the example shown, the vehicle 60 may be illustrated as a vehicle with three rows of seats (e.g., the front row comprising the seats 90a-90b and the seat rows 92a-92b). In the example shown, the seats 90a-90b and the seat rows 92a-92b are shown facing forward (e.g., towards a front end of the vehicle 60). In some embodiments, one or more of the seats 90*a*-90*b* and/or individual seats in the seat rows 92*a*-92*b* may face forward, backwards, may be rotated at an angle, may be upright, may be reclined, etc. The arrangement of the people 70*a*-70*d* in the seats 90*a*-90*b* and/or the seat rows 92*a*-92*b*, the number of seats, the location of seats and/or the arrangement of seats in the vehicle 60 may be varied according to the design criteria of a particular implementation.

The radar units 100*a*-100*b* are shown in the interior 62 of the vehicle 60. The radar units 100*a*-100*b* may be configured to detect a presence of the people 70*a*-70*d* in the interior 62. The radar units 100*a*-100*b* may be configured to operate while the vehicle 60 is turned on (e.g., powered on, driving, idling, etc.). The radar units 100*a*-100*b* may be configured to operate while the vehicle 60 is turned off (e.g., powered off, parked, etc.).

In the example shown, the interior 62 of the vehicle 60 may comprise two of the radar units 100*a*-100*b*. Generally, the radar units 100*a*-100*b* may be installed in the vehicle 60 such that one of the radar units 100*a*-100*n* is implemented per every two rows of seats of the vehicle 60. In the example shown, the vehicle 60 may comprise three rows of seats (e.g., the seats 90*a*-90*b* and two additional seat rows 92*a*-92*b*). In order to accommodate three rows of seats, the two radar units 100*a*-100*n* may be implemented. In an embodiment of the vehicle 60 with two rows of seats (e.g., a sedan type vehicle) one of the radar units 100*a*-100*n* may be installed. Additional radar units 100*a*-100*n* (or fewer of the radar units 100*a*-100*n*) may be implemented depending on a layout of the interior 62, the number and/or arrangement of obstacles in the interior 62, different numbers of seat rows, an amount of space in the interior 62, etc. In an example, a mass transit vehicle (e.g., a city bus, a school bus, etc.) may implement five or more of the radar units 100*a*-100*n* to ensure people are not left on the mass transit vehicle. The number of radar units 100*a*-100*n* implemented and/or the installation location of the radar units 100*a*-100*n* may be varied according to the design criteria of a particular implementation.

The radar units 100*a*-100*n* may be configured to detect and/or distinguish between the people 70*a*-70*d* in the interior 62. The radar units 100*a*-100*n* may be configured to determine a number of the people 70*a*-70*d* and/or a location of the people 70*a*-70*d* in the interior 62. The radar units 100*a*-100*n* may be configured to determine characteristics of the people 70*a*-70*d* in the interior 62. In the example shown, the radar units 100*a*-100*b* may detect the person 70*a* and the characteristics of the person 70*a* in the driver seat 90*a*, the person 70*b* and the characteristics of the person 70*b* in the passenger seat 90*b*, the person 70*c* and the characteristics of the person 70*c* in the seat row 92*a* and the person 70*d* and the characteristics of the person 70*d* in the seat row 92*b*.

The characteristics of the people 70*a*-70*d* detected by the radar units 100*a*-100*n* may comprise biomarkers, shape and size information and/or other readings about the people 70*a*-70*d*. The characteristics may comprise any feature of the people 70*a*-70*d* that may be used by the radar units 100*a*-100*n* (or other components of the vehicle 60) to infer information about the people 70*a*-70*d* detected. In one example, the characteristics of the people 70*a*-70*d* detected by the radar units 100*a*-100*n* may be used to infer an age range of each of the people 70*a*-70*d*. In another example, the characteristics of the people 70*a*-70*d* detected by the radar units 100*a*-100*n* may be used to infer a status of each of the people 70*a*-70*d* (e.g., awake, asleep, in distress, etc.). In yet another example, the characteristics of the people 70*a*-70*d* detected by the radar units 100*a*-100*n* may be used to infer a body position of each of the people 70*a*-70*d* (e.g., sitting upright, leaning against a window, lying down, etc.). The types of characteristics detected and/or the inferences about the people 70*a*-70*d* determined in response to the characteristics detected by the radar units 100*a*-100*n* may be varied according to the design criteria of a particular implementation.

The radar units 100*a*-100*n* may be configured to compare (or provide information for a comparison) of the detected characteristics of the people 70*a*-70*d* to known characteristics of particular groups of people. In one example, the characteristics detected by the radar units 100*a*-100*n* may be compared against known biometric information about particular categories of people (e.g., biometric information for awake adults, biometric information for sleeping adults, biometric information for awake children, biometric information for sleeping children, etc.).

One of the characteristics detected by the radar units 100*a*-100*n* may comprise a body size and/or shape. In an example, a body size and/or shape of the person 70*a* detected by the radar unit 100*a* may be compared to known body sizes for particular age groups (e.g., shapes and sizes of male and female adults, shapes and sizes of male and female teenagers, shapes and sizes of male and female children, shapes and sizes for male and female infants, etc.). One of the characteristics detected by the radar units 100*a*-100*n* may comprise a heart beat rate. In an example, a heart beat rate of the person 70*c* detected by the radar unit 100*a* may be compared to known heart beat rates for particular age groups (e.g., known heart beat rates for male and female adults, known heart beat rates for male and female children, known heart beat rates for male and female infants, etc.).

One of the characteristics detected by the radar units 100*a*-100*n* may comprise a breathing rate. In an example, a breathing rate of the person 70*d* detected by the radar unit 100*b* may be compared to known breathing rates for particular age groups (e.g., known breathing rates for male and female adults, known breathing rates for male and female children, known breathing rates for male and female infants, etc.).

One of the characteristics detected by the radar units 100*a*-100*n* may comprise a temperature. The temperature measurement may be used to determine a temperature of each of the people 70*a*-70*d* and/or an ambient temperature within the vehicle 60. The temperature measured by the radar units 100*a*-100*n* may be used to determine whether the people 70*a*-70*d* are experiencing extreme temperature conditions (e.g., conditions that may potentially cause harm to the people 70*a*-70*d* based on an amount of exposure).

The radar units 100*a*-100*n* may provide information about multiple characteristics detected. For example, whether the person 70*b* is a child or an adult (or a particular age range of the person 70*b*) may be determined by analyzing the shape of the person 70*b* and the heart beat rate of the person 70*b*. In another example, whether the person 70*c* is a child or an infant (or a particular age range of the person 70*c*) may be determined by analyzing the shape of the person 70*c* and the breathing rate of the person 70*c*.

In the example shown, the passengers 70*a*-70*d* may comprise people. Generally, the characteristics of the people 70*a*-70*d* detected and/or information inferred about the people 70*a*-70*d* may be applicable to human passengers. The radar units 100*a*-100*n* may be configured to determine characteristics and/or infer information about other types of living beings (e.g., dogs, cats, etc.). For example, the radar units 100*a*-100*n* may be configured to detect the presence and/or categorize pets within the interior 62.

Figure 3:
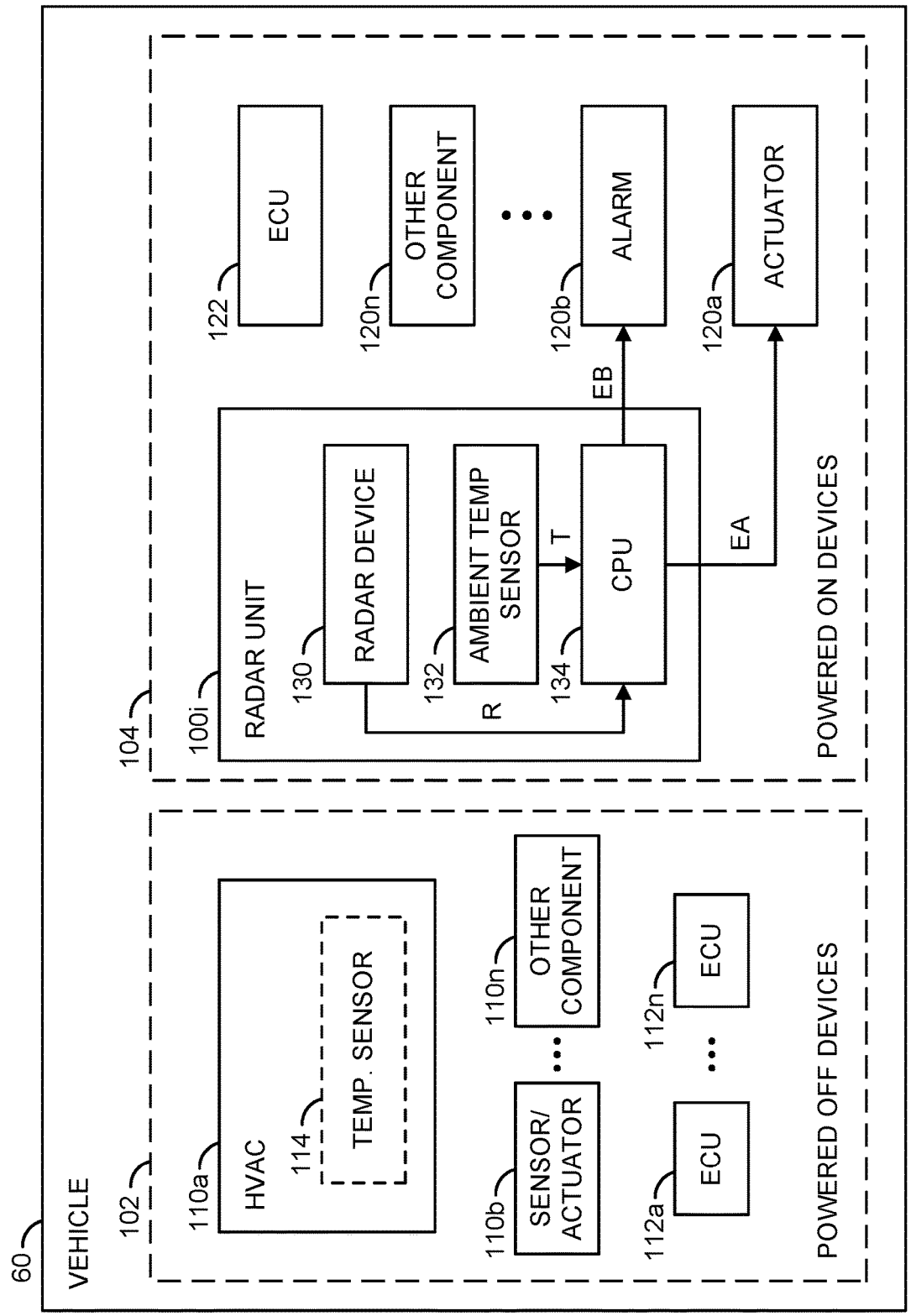
FIG. 3 is a block diagram illustrating an example embodiment of the present invention.

Referring to FIG. 3, a block diagram illustrating an example embodiment of the present invention is shown. Various components of the vehicle 60 are shown. The vehicle 60 is shown comprising a category of components 102 and/or a category of components 104. The category of components 102 may comprise components that may be powered off when the vehicle 60 is turned off. The category of components 104 may comprise components that may remain powered on after the vehicle 60 is turned off. In some embodiments, some of the components 104 that may remain powered on after the vehicle 60 is turned off may remain powered on for a temporary amount of time and then turn off after the amount of time has elapsed (e.g., change from one of the powered on devices 104 to the powered off devices 102). In the example shown, the vehicle 60 may be turned off. The components shown may be an illustrative example. Which components are powered on, which components are powered off and/or a length of time that particular components remain powered on after the vehicle 60 is turned off may be varied according to the design criteria of a particular implementation.

The powered off devices 102 may comprise blocks (or circuits) 110a-110n and/or blocks (or circuits) 112a-112n. The circuits 110a-110n may comprise various components. The circuits 112a-112n may comprise various electronic control units (ECUs). The number, type and/or functionality of the powered off devices 102 may be varied according to the design criteria of a particular implementation.

The components 110a-110n may comprise various devices, sensors, actuators and/or systems of the vehicle 60 that may be powered off while the vehicle 60 is powered off. In an example, one or more of the components 110a-110n that may be powered off may be a lighting system. In another example, one or more components 110a-110n that may be powered off may be a camera system. In yet another example, one or more components 110a-110n that may be powered off may be an infotainment system. Generally, the components 110a-110n that may be turned off when the vehicle 60 is turned off may correspond to driving systems, driver assistance systems, and/or comfort systems.

The ECUs 112a-112n may be configured to manage and/or perform calculations for various systems and/or components of the vehicle 60. The ECUs 112a-112n may be configured to receive input from various sensors, perform calculations, make determinations/decisions (e.g., interpret data) and/or generate signals to activate actuators of the vehicle 60. The ECUs 112a-112n may be configured to control specific functionality of the vehicle 60. In an example, the ECUs 112a-112n may control essential functionality (e.g., engine, braking, power steering control, etc.). In another example, the ECUs 112a-112n may control comfort features (e.g., power windows, seats position, HVAC, infotainment, etc.). In yet another example, the ECUs 112a-112n may control security and access to the vehicle 60 (e.g., door locks, keyless entry, etc.). In still another example, the ECUs 112a-112n may control passive and/or active safety features (e.g., airbags, automatic emergency braking, seatbelt restraints, etc.). The types of features controlled by the ECUs 112a-112n may be varied according to the design criteria of a particular implementation.

The ECUs 112a-112n may comprise a processor and/or a memory. In some embodiments, the ECUs 112a-112n may implement application specific integrated circuits (ASIC) and/or a system on a chip (SoC). Generally, the ECUs 112a-112n may comprise dedicated circuitry that runs software or firmware and requires power and data connections to operate. The ECUs 112a-112n may be powered off (e.g., control features that are considered unnecessary while the vehicle 60 is powered down).

In the example shown, the component 110a may represent a heating and cooling system (a Heating, ventilation, and air conditioning (HVAC) system). The HVAC 110a may be a high power consuming component. For example, to prevent excessive power consumption, the HVAC 110a may be turned off while the vehicle 60 is powered down.

The HVAC 110a may comprise a block (or circuit) 114. The HVAC 110a may comprise other components (not shown). The circuit 114 may implement an HVAC temperature sensor. The HVAC temperature sensor 114 may be configured to measure temperature in the interior 62 to provide input for the HVAC 110a to control the temperature in the interior 62. Since the HVAC 110a may be one of the powered off devices 102, the HVAC temperature sensor 114 may not be operational while the vehicle 60 is powered off. Even if the HVAC 110a was not powered off, the HVAC temperature sensor 114 may not provide reliable temperature measurements while the vehicle 60 is parked (e.g., HVAC temperature sensors rely on the flow of air in the air vents to measure temperature and vehicles that are not moving have less air flow through the air vents).

The powered on devices 104 may comprise the radar units 100a-100n (e.g., the radar unit 100i is shown as a representative example for illustrative purposes), blocks (or circuits) 120a-120n and/or a block (or circuit) 122. The circuits 120a-120n may comprise various components. The circuit 122 may comprise an ECU. The number, type and/or functionality of the powered on devices 104 may be varied according to the design criteria of a particular implementation.

The components 120a-120n may comprise various devices, sensors, actuators and/or systems of the vehicle 60 that may be powered on while the vehicle 60 is powered on. In the example shown, the component 120a may be an actuator and the component 120b may be an alarm. In one example, the components 120a-120n may be configured to provide essential features. Generally, the components 120a-120n may be low power consumption devices (e.g., to prevent excessive battery drain). In an example, one or more of the components 120a-120n that may be powered on while the vehicle 60 is turned off may be security systems (e.g., the alarm 120b may provide alerts as an output and other of the components 120a-120n may be comprise sensors configured to perform proximity detection, entry detection, etc.). In another example, one or more of the components 120a-120n that may be powered on may comprise wireless communication devices (e.g., to receive remote unlock signals, remote car starting, communicate status information, etc.). One or more of the components 120a-120n that may be powered on may operate in a sleep or low-powered state (e.g., a remote rear hatch actuator may not consume power, but may be activated in response to a remote door open signal). Generally, the components 120a-120n that may be turned on when the vehicle 60 is turned off may correspond to security systems, warning systems, and/or vehicle systems. The types of the components 120a-120n and/or the functionality of the components 120a-120n may be varied according to the design criteria of a particular implementation.

The ECU 122 may implement similar functionality and/or may have a similar implementation as the ECUs 112a-112n. The ECU 122 may be powered on while the vehicle 60 is turned off in order to enable the functionality of the components 120a-120n that remain powered on. For example, the ECU 122 may be configured to receive input from the radar units 100a-100n and/or other sensors. The ECU 122 may be configured to interpret the data received and generate output signals to activate the components 120a-120n that provide actuator functionality. In the example shown, a single ECU 122 is shown as one of the powered on devices 104 for illustrative purposes. More than one ECU may remain powered on while the vehicle 60 has been turned off.

The radar unit 100i may comprise a block (or circuit) 130, a block (or circuit) 132 and/or a block (or circuit) 134. The circuit 130 may implement a radar device. The circuit 132 may implement an ambient temperature sensor. The circuit 134 may implement a processor (e.g., a CPU, a SoC, etc.). The radar unit may comprise other components (not shown). The number, type and/or arrangement of the components of the radar units 100a-100n may be varied according to the design criteria of a particular implementation.

The radar device 130 may be configured to generate and/or read radar signals. The radar device 130 may be configured to interpret the data from the radar signals (e.g., a Doppler effect). The radar device 130 may be configured to detect and/or validate a presence of the people 70a-70d in the interior 62. The radar device 130 may be configured to determine characteristics of the people 70a-70d (e.g., the shape, the size, the heart beat rate, the breathing rate, etc.). The data from the radar device 130 may be used to determine an age range and/or a location of the people 70a-70d in the interior 62. The radar device 130 may be configured to provide the radar data (e.g., information about the presence of the people 70a-70d) to the processor 134.

In the example shown, the radar units 100a-100n may implement the radar device 130 to perform the detection and/or verification of the presence of the people 70a-70d and/or determine the characteristics of the people 70a-70d. In some embodiments, alternate types of sensors may be implemented (e.g., instead of the radar device 130 or as complementary sensors to the radar device 130 to provide multiple disparate sources of detection). In one example, the presence and/or detection of characteristics of the people 70a-70d may be measured using ultrasonic sensors. In another example, the presence and/or detection of characteristics of the people 70a-70d may be measured using cameras (e.g., computer vision). The type of measurements used to perform the presence and/or detection of characteristics of the people 70a-70d may be varied according to the design criteria of a particular implementation.

The ambient temperature sensor 132 may be configured to determine an ambient temperature in the interior 62. In some embodiments, the ambient temperature sensor 132 may be configured to measure a body temperature of each of the people 70a-70d. The ambient temperature sensor 132 may be implemented by each of the radar units 100a-100n to enable operation that may be independent from the heating and cooling system 110a of the vehicle 60. The ambient temperature sensor 132 may operate independently from other temperature measuring components of the vehicle 60. The ambient temperature sensor 132 may be configured to provide an ambient temperature measurement to the processor 134.

In some embodiments, the processor 134 may be a component of each of the radar units 100a-100n. The processor 134 may be configured to determine an urgency level of the conditions in the interior 62 in response to the age range of the people 70a-70d detected (e.g., the input from the radar device 130) and the ambient temperature measurement (e.g., the input from the ambient temperature sensor 132). The processor 134 may be configured to generate one or more output signals. The output signals generated by the processor 134 may be presented to one or more of the components 120a-120n. In the example shown, one output signal may be presented to the actuator 120a and one output signal may be presented to the alarm 120b. The output signals from the processor 134 may be generated independently or simultaneously.

The processor 134 may be configured to determine an urgency level in response to the people 70a-70d detected and/or the ambient temperature measurement. The urgency level may comprise an evaluation of the environmental conditions within the interior 62. In some embodiments, the urgency level may comprise fuzzy logic. The processor 134 may use the evaluation of the urgency level to determine the type of response to perform. In an example, if the urgency level indicates no or minimal threat to the people 70a-70d, the processor 134 may determine that no response may be performed. In another example, if the urgency level indicates a moderate threat to the people 70a-70d, the processor 134 may determine that the alert 80 may be generated. In yet another example, if the urgency level indicates a high threat to the people 70a-70d, the processor 134 may determine that an alternate intervention may be initiated. The number and/or thresholds for each of the urgency levels evaluated by the processor 134 and/or the factors that constitute a threat to the people 70a-70d may be varied according to the design criteria of a particular implementation.

The processor 134 may be configured to determine escalating actions (or responses) to perform and/or enable based on the urgency level. The escalating responses may comprise outputs generated by the processor 134 that perform increasing amounts of intervention and/or draw increasing amounts of attention from a vehicle owner (or people near the vehicle 60) that correspond to the urgency level determined. The output signal(s) generated by the processor 134 may be configured to generate the escalating actions in response to the urgency level.

The radar device 130 may be configured to present a signal (e.g., R) to the processor 134. The signal R may represent the radar data generated by the radar device 130. The ambient temperature sensor 132 may be configured to present a signal (e.g., T) to the processor 134. The signal T may represent the ambient temperature measured by the ambient temperature sensor 132. The processor 134 may be configured to present signals (e.g., EA-EB) to a respective one of the components 120a-120b. The signals EA-EB may comprise control signals configured to enable the components 120a-120b to perform one or more of the escalating responses.

The radar units 100a-100n may be configured to operate when the vehicle 60 is turned off. The radar units 100a-100n, and the ambient temperature sensor 132, may be configured to be operational while the HVAC system 110a is powered off. In some embodiments, the radar units 100a-100n may be configured to remain on an entire time that the vehicle 60 is powered off. In some embodiments, the radar units 100a-100n may be configured to remain on for a predetermined amount of time after the vehicle 60 is powered off. For example, the ambient temperature sensor 132 may be configured to measure the ambient temperature continually (or continuously) for a predetermined amount of time after the vehicle 60 is turned off.

In some embodiments, the radar units 100a-100n may be configured to cycle between a powered on state and a sleep (or low power, or off) state. In an example, the temperature sensor 132 may be configured to measure the ambient temperature in the interior 62 for a particular amount of time. For example, the radar units 100a-100n may remain off for an activation amount of time after the vehicle 60 is turned off (e.g., the radar units 100a-100n may remain on for five minutes after the vehicle 60 is off to enable the radar device 130 to detect the presence of the people 70a-70d and for the ambient temperature sensor 132 to measure the ambient temperature). After the activation amount of time, the radar units 100a-100n may be powered off (or enter a sleep state). The radar units 100a-100n may be powered off for a sleep interval (e.g., a predetermined amount of time). After the sleep interval has elapsed, the radar units 100a-100n may be powered on for a measurement time period. During the measurement time period, the radar device 130 may detect the presence and/or update the characteristics of the detected people 70a-70d (e.g., determine whether a breathing rate or heart beat rate has changed, which may indicate worsening conditions). During the measurement time period, the ambient temperature sensor 132 may measure the ambient temperature. After the measurement time period, the radar units 100a-100n may return to the powered off state.

The radar units 100a-100n may cycle between the powered off state for the sleep interval and the powered on state for the measurement time period. In some embodiments, the radar units 100a-100n may cycle between the powered off/on states for the entire time that the vehicle 60 is turned off. In some embodiments, the radar units 100a-100n may cycle between the powered off/on states for a particular amount of time while the vehicle 60 is turned off (e.g., one hour, two hours, half an hour, etc.). The amount of time that the radar units 100a-100n remain on after the vehicle 60 is turned off, the amount of time for the sleep interval, the amount of time for the time measurement period and/or the amount of time to repeat the powered on/off cycles may each be different. The amount of the various times may be varied according to the design criteria of a particular implementation.

The urgency level may be determined by the processor 134 based on various factors. The factors may comprise the age range of the detected people 70a-70d, the current ambient temperature measurement, a rate of change of the ambient temperature measurement and/or a length of exposure to the ambient temperature measured. The urgency level may have an upper threshold temperature (e.g., too hot in the vehicle 60) and a lower threshold temperature (e.g., too cold in the vehicle 60). In an example, exceeding either the upper threshold temperature or the lower temperature level may result in the processor 134 determining the highest urgency level. In an example, exceeding the lower threshold temperature or the upper threshold temperature may result in the highest urgency level regardless of the age range or the determined capacity of the detected people 70a-70d (e.g., the conditions may be too extreme for anybody). Lower urgency levels may be selected by weighting the various factors. Age range may be one factor for determining the urgency level. In an example, a notification and/or an alert may be generated in response to a child detected alone in the vehicle 60 (e.g., a person age six or younger). In some embodiments, the urgency level may be increased or decreased regardless of the age range of the detected people 70a-70d.

In some embodiments, the urgency level may be adjusted in response to the other people detected in the vehicle 60. In an example, if the detected person 70d is determined to be a child and was alone in the vehicle 60, then a higher urgency level may be determined by the processor 134. In another example, if the same detected person 70d (e.g., a child) is detected in the vehicle along with an adult occupant (e.g., an adult 70a), then the urgency level may be reduced (e.g., the adult may be capable of opening the car doors, turning on the HVAC 110a, tending to the child, etc.). A high urgency level may still be determined even with an adult present based on the characteristics detected (e.g., the child 70d has a very low heart beat rate, a low breathing rate, the temperature is extreme, etc.).

In one example, at least three urgency levels may be implemented. A first (e.g., lowest) urgency level may be determined when the person (e.g., 70c) is a child left alone in the vehicle 60 and the ambient temperature measurement is a comfortable temperature (e.g., between the upper threshold temperature and the lower threshold temperature and the temperature is decreasing or increasing at a low rate). In response to the low urgency level, one of the escalating responses may be performed (e.g., a response with low intrusiveness, such as an alert/notification may be sent to a smartphone indicating that a child is alone in the vehicle 60). A second (e.g., medium) urgency level may be determined when the person (e.g., 70c) is a child left alone in the vehicle 60 and the ambient temperature is below the upper threshold and increasing at a high rate or above the lower threshold and decreasing at a high rate (e.g., the current temperature is comfortable but increasing towards the upper threshold or decreasing towards the lower threshold). In response to the medium urgency level, one of the escalating responses may be performed (e.g., a response with a higher amount intrusiveness). For example, the processor 134 may activate the alarm 120b to generate the alert 80. A third (e.g., high) urgency level may be determined when the person (e.g., 70c) is a child left alone in the vehicle 60 and the ambient temperature is above said upper threshold or below said lower threshold. In response to the high urgency level, one of the escalating responses may be performed (e.g., the most intrusive types of responses, such as opening a vehicle window, unlocking all the doors (even at the cost of vehicle security), activating the HVAC 110a, contacting emergency services, etc.).

The actuators 120b may be one example actuator that may be configured to perform the various escalating actions (e.g., lowering the windows, unlocking the car door, enabling the HVAC 110a). In an example, the processor 134 may be configured to activate one or more actuators in response to the urgency level. In some embodiments, the processor 134 may be configured to provide input to the ECU 122 and the ECU 122 may enable the various components 120a-120n to perform the various escalating actions.

Figure 4:
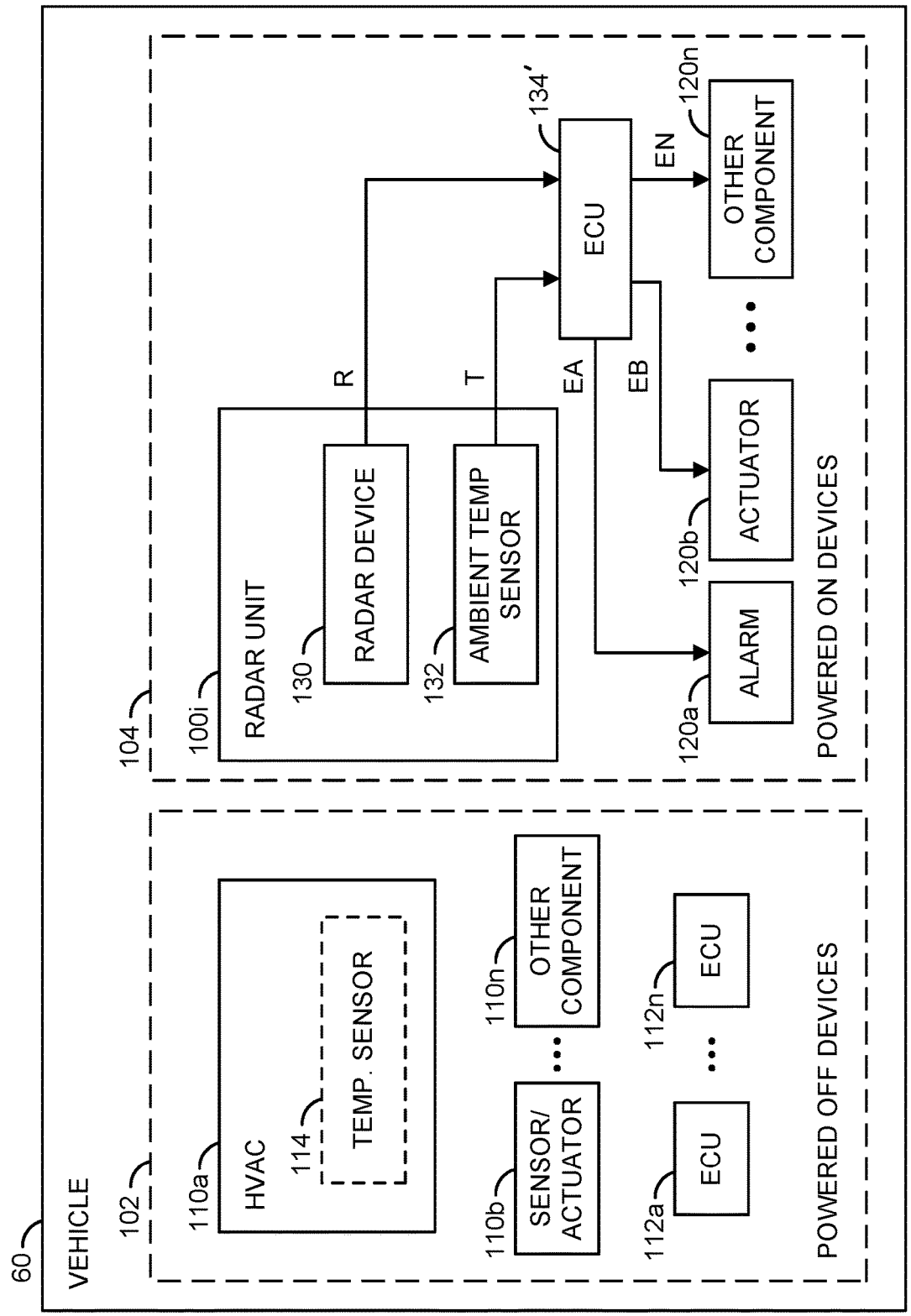
FIG. 4 is a block diagram illustrating an alternate embodiment of the present invention.

Referring to FIG. 4, a block diagram illustrating an alternate embodiment of the present invention is shown. The block diagram of the vehicle 60 may be similar to the block diagram described in association with FIG. 3. The HVAC 110a and the other components 110b-110n and the ECUs 112a-112n may be the powered off devices 102. Similarly, the radar units 100a-100n and/or the components 120a-120n may be the powered on devices 104.

In some embodiments, the radar units 100a-100n may be implemented without the processor 134. In the example shown, the radar unit 100i may comprise the radar device 130 and the ambient temperature sensor 132. The radar device 130 may provide the presence detection information and/or the characteristic information to an external device. The ambient temperature sensor 132 may provide the ambient temperature measurement to an external device. The external device may determine the urgency level and/or the escalating responses.

In the example shown, the radar unit 100i may provide the output to the ECU 134'. The ECU 134' may comprise a processor configured to perform functionality similar to the processor 134 described in association with FIG. 3. The ECU 134' may be configured to receive an input from the radar component 130 (e.g., the signal R) and an input from the ambient temperature sensor 132 (e.g., the signal T).

The ECU 134' may be configured to receive input and/or provide output (e.g., the signals EA-EN) to the powered on components 120*a*-120*n*. In some embodiments, the ECU 134' may be configured to activate one or more of the components 120*a*-120*n* in response to only input from one or more of the radar units 100*a*-100*n* (e.g., the ECU 134' may be a dedicated ECU for the radar units 100*a*-100*n*). In some embodiments, the ECU 134' may be configured to activate one or more of the components 120*a*-120*n* in response to input from the radar units 100*a*-100*n* and/or other of the components 120*a*-120*n* (e.g., the ECU 134' may be configured to make determinations based on multiple systems within the vehicle 60).

In some embodiments, the ECU 134' may be configured to receive the ambient temperature measurement from the temperature sensor 132 and receive other temperature measurements from other of the powered on devices 104 (not shown). The processor implemented by the ECU 134' may be configured to perform a weighted average of the ambient temperature and the other temperature information. The processor implemented by the ECU 134' may determine the urgency level based on the weighted average calculated. Determining the weighted average based on multiple disparate sources of temperature information may prevent distorted readings (e.g., measuring hot spots or cold spots in the vehicle 60 when the overall temperature is different).

Figure 5:
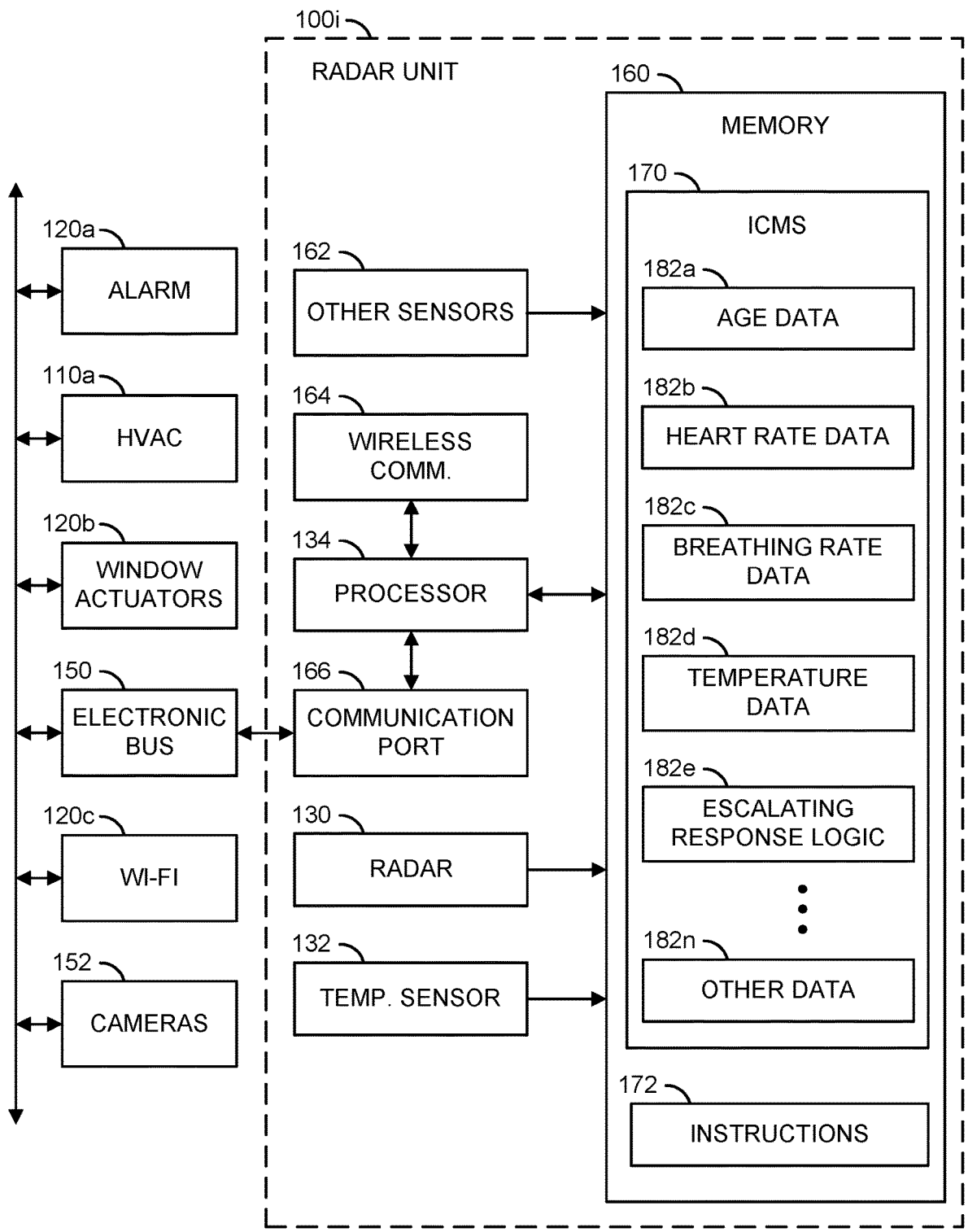
FIG. 5 is a block diagram illustrating components of a vehicle that may be activated as escalating responses to a detected urgency level.

Referring to FIG. 5, a block diagram illustrating components of a vehicle that may be activated as escalating responses to a detected urgency level is shown. The radar unit 100*i* is shown as a representative example of any of the radar units 100*a*-100*n*. The radar unit 100*i* is shown connected to an electronic bus 150.

The electronic bus 150 may be configured to enable various components within the vehicle 60 to exchange data. The electronic bus 150 may be bi-directional to enable the radar units 100*a*-100*n* to send and/or receive data to/from other components. In one example, the electronic bus 150 may be a CAN bus.

Various components are shown communicating on the electronic bus 150. In the example shown, the HVAC 110*a*, the alarm 120*a*, window actuators 120*b*, wireless communications (e.g., Wi-Fi, Bluetooth, ZigBee, etc.) may communicate over the electronic bus 150. A block (or circuit) 152 is shown connected to the electronic bus 150. In the example shown, the circuit 152 may comprise a camera system (e.g., blindspot cameras, cameras used for autonomous driving, etc.). The components communicating over the electronic bus 150 may comprise the powered off devices 102 and/or the powered on devices 104. For example, the electronic bus 150 may enable the radar units 100*a*-100*n* to activate the HVAC 110*a* as one of the escalating responses.

The radar unit 100*i* is shown comprising the radar device 130, the ambient temperature sensor 132, the processor 134, a block (or circuit) 160, a block (or circuit) 162, a block (or circuit) 164 and/or a block (or circuit) 166. The circuit 160 may implement a memory. The circuit 162 may implement other sensors. The circuit 164 may implement wireless communications. The circuit 166 may implement a communication port. The radar units 100*a*-100*n* may comprise other components (not shown). The number, type and/or arrangement of the components of the radar units 100*a*-100*n* may be varied according to the design criteria of a particular implementation.

The memory 160 may comprise a block (or circuit) 170 and/or a block (or circuit) 172. The circuit 170 may comprise ICMS storage. The circuit 172 may comprise computer readable instructions. The memory 160 may be configured to store data presented by the radar device 130, the temperature sensor 132, the processor 134 and/or the other sensors 162. The memory 160 may be configured to provide stored data and/or the computer readable instructions to the processor 134.

The radar units 100*a*-100*n* may be configured to generate presence information (e.g., from the radar device 130) and/or ambient temperature measurements (e.g., from the ambient temperature sensor 132). The radar units 100*a*-100*n* may implement other sensors 162. The other sensors 162 may be configured to perform other types of measurements that may be relevant to determining the conditions within the interior 62 and/or the presence of the people 70*a*-70*d* (e.g., camera data, pressure, humidity, ultrasonic data, etc.).

The wireless communications 164 may enable the radar units 100*a*-100*n* to communicate wirelessly. The wireless communications 164 may implement one or more wireless communications protocols (e.g., GNSS, Wi-Fi, Bluetooth, ZigBee, NFC, etc.). The wireless communications 164 may be configured to receive information from external sources and/or communicate data to the external sources. In one example, the wireless communications module 164 may be configured to communicate with a smartphone. In one example, the wireless communications 164 may be configured to determine a distance from the vehicle 60 of the smartphone. In another example, the wireless communications 164 may be configured to communicate warnings and/or notifications to the smartphone as one of the escalating responses (e.g., send a notification that a child has been left alone in the vehicle 60).

The communication port 166 may comprise a wired connection. The communication port 166 may be configured to enable communication via the electronic bus 150. The communication port 166 may enable the processor 134 to send/receive data over the electronic bus 150 to communicate with the components 120*a*-120*n* and/or the ECU 122. In some embodiments, the communication port 166 may enable the processor 134 to activate one or more of the disabled (or powered down) devices 110*a*-110*n* and/or ECUs 112*a*-112*n*. For example, one of the escalating actions may be to activate the HVAC 110*a* in response to the urgency level.

The ICMS storage 170 may be configured to store data for the ICMS features. The ICMS storage 170 may comprise blocks (or circuits) 182*a*-182*n*. The blocks 182*a*-182*n* may store various data sets. For example, the data sets 182*a*-182*n* may comprise age data 182*a*, heart rate data 182*b*, breathing rate data 182*c*, temperature data 182*d*, escalating response logic 182*e* and/or other data 182*n*.

The processor 134 may be configured to execute stored computer readable instructions (e.g., the instructions 172 stored in the memory 160). The processor 134 may perform one or more steps based on the stored instructions 172. In an example, one of the steps of the instructions 172 executed/performed by the processor 134 may analyze the characteristics of the detected people 70*a*-70*d* and read the ambient temperature measurement. In another example, one of the steps of the instructions 172 may be executed/performed by the processor 134 may determine the urgency level. In yet another example, one of the steps of the instructions 172 may be executed/performed by the processor 134 and may determine the escalating responses to perform in response to the urgency level. In still another example, one of the steps of the instructions 172 may be executed/performed by the processor 134 and may cycle between the sleep and powered on mode of operation. The instructions executed and/or the order of the instructions 172 performed by the processor 134 may be varied according to the design criteria of a particular implementation.

The age data 182a may comprise information about characteristics that may be commonly associated with various age groups. The age data 182a may be used by the processor 134 to compare against the characteristics measured by the radar device 130. In an example, the age data 182a may comprise biometric information about breathing rates and/or heart rates that may be associated with particular types of people (e.g., age ranges, genders, body type, body size, etc.). The age data 182a may comprise statistical information about different types of people. The age data 182a may enable the processor 134 to compare against the characteristics to determine whether any of the detected people 70a-70d are infants, children, teenagers, adults, elderly, over a particular age, below a particular age, in between limits of an age range, etc. The granularity of the various age ranges may be varied according to the amount of statistical information available.

The heart rate data 182b may comprise information about the heart rates of the detected people 70a-70d. The heart rate data 182b may be provided by the radar device 130. In an example, the heart rate data 182b may be stored about each of the detected people 70a-70d. In some embodiments, the heart rate data 182b may be stored according to a time of measurement to enable the heart rates detected to be monitored over time (e.g., to determine potential issues with rapidly increasing heart rates or decreasing rates). The heart rate data 182b may be used by the processor 134 to compare against the age data 182a (e.g., known heart beat rates) in order to determine the age range and/or other characteristics of the people 70a-70d.

The breathing rate data 182c may comprise information about the breathing rates of the detected people 70a-70d. The breathing rate data 182c may be provided by the radar device 130. In an example, the breathing rate data 182c may be stored about each of the detected people 70a-70d. In some embodiments, the breathing rate data 182c may be stored according to a time of measurement to enable the breathing rates detected to be monitored over time (e.g., to determine potential issues if a person stops breathing, has shallow breaths, is hyperventilating, etc.). The breathing rate data 182c may be used by the processor 134 to compare against the age data 182a (e.g., known breathing rates) in order to determine the age range and/or other characteristics of the people 70a-70d.

The temperature data 182d may comprise information about the ambient temperature in the interior 62. The temperature data 182d may be provided by the temperature sensor 132. In an example, the temperature data 182d may be stored according to time of measurement to enable the processor 134 to determine the rate of temperature change and/or determine a length of time of exposure for each of the detected people 70a-70d. In some embodiments, the temperature data 182d may comprise input from sensors data communicated over the electronic bus 150 (e.g., data from temperature sensors of the powered on components 120a-120n) to provide data for the processor 134 to perform the weighted average calculations for the temperature measurements.

The escalating response logic 182e may comprise information about the various conditions that correlate to particular urgency levels and/or the types of escalating responses to perform in response to particular urgency levels. In an example, the processor 134 may receive the heart rate data 182b, the breathing rate data 182c to compare against the age data 182a, and receive the temperature data 182d to determine the environmental factors. The results calculated by the processor 134 may be compared to the escalating response logic 182e. The escalating response logic 182e may comprise a look up table of temperature thresholds for particular age groups and/or particular animal types. The processor 134 may be configured to evaluate the urgency level based on the information stored in the response logic 182e (e.g., how long a person may be exposed to a particular temperature, which temperature rates indicate a high or lower urgency level, which breathing rates indicate danger, which heart rates indicate danger, etc.).

The escalating response logic 182e may further comprise the types of escalating actions to perform in response to particular urgency levels and/or conditions detected. The escalating response logic 182e may comprise information about which of the components 120a-120n are available for performing the escalating actions. In one example, the escalating response logic 182e may indicate that a cooling system should be activated in response to a high temperature threshold being exceeded. In another example, the escalating response logic 182e may indicate that a heating system should be activated in response to a low temperature threshold being exceeded. In yet another example, the escalating response logic 182e may indicate who to contact to provide a low level warning in response to a low urgency level (e.g., a smartphone number or device ID).

The other data 182n may comprise other data that may be relevant to determining the characteristics of the people detected 70a-70d, determining the urgency level, determining the escalating actions to perform and/or determining which components are available for performing the escalating actions. In one example, the other data 182n may comprise shape and/or size information detected about people 70a-70d by the radar device 130. In another example, the other data 182n may comprise statistical shape and/or size information about various age groups, people and/or animals that may be used by the processor 134 to compare against the detected people 70a-70d. The types of data stored by the other data 182n may be varied according to the design criteria of a particular implementation.

Figure 6:
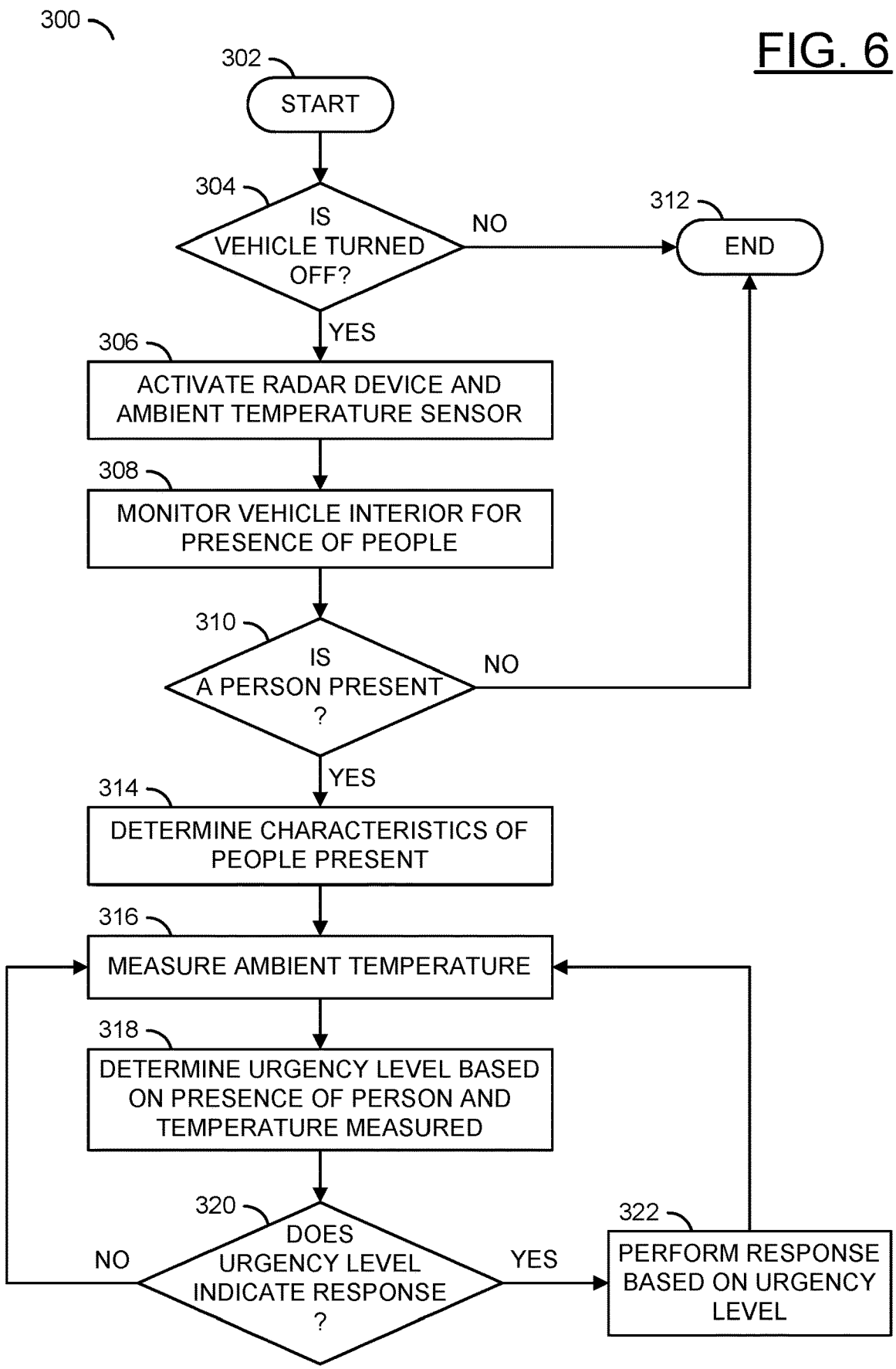
FIG. 6 is a flow diagram illustrating a method for in-cabin temperature monitoring for child presence detection.

Referring to FIG. 6, a method (or process) 300 is shown. The method 300 may implement in-cabin temperature monitoring for child presence detection. The method 300 generally comprises a step (or state) 302, a decision step (or state) 304, a step (or state) 306, a step (or state) 308, a decision step (or state) 310, a step (or state) 312, a step (or state) 314, a step (or state) 316, a step (or state) 318, a decision step (or state) 320, and a step (or state) 322.

The step 302 may start the method 300. Next, the method 300 may move to the decision step 304. In the decision step 304, the radar units 100a-100n may determine whether the vehicle 60 has been turned off. In an example, the processor 134 and/or the ECU 134' may read a vehicle status (e.g., on/off) from the electronic bus 150. If the vehicle is on, then the method may move to the step 312 (e.g., monitoring using the radar device 130 and/or the ambient temperature sensor 132 for performing escalating responses in response to the urgency level may not be performed). If the vehicle is off, then the method 300 may move to the step 306.

In the step 306, the radar units 100a-100n may activate the radar device 130 and the ambient temperature sensor 132. In some embodiments, the radar device 130 and/or the ambient temperature sensor 132 may already be active while the vehicle 60 is turned on (e.g., to implement other types of functionality, such is driver monitoring, passenger location, etc.). In some embodiments, the radar device 130 and/or the ambient temperature sensor 132 may be turned off while the vehicle 60 is on (e.g., driving) and may be powered on while the vehicle 60 is off. Next, in the step 308, the radar device 130 may monitor the interior 62 of the vehicle 60 for the presence of the people 70a-70d. For example, the radar device 130 may convert the measurements to an electrical signal and provide the electrical signal R comprising the sensor readings to the processor 134 and/or the ECU 134'. Next, the method 300 may move to the decision step 310.

In the decision step 310, the processor 134 (or the ECU 134') may determine whether a person is present. For example, the processor 134 may read and/or interpret the sensor readings from the radar device 130 to determine whether the interior 62 has living beings present or not. If no person is present, then the method 300 may move to the step 312. The step 312 may end the method 300. For example, if none of the people 70a-70d are present, further monitoring (e.g., ambient temperature measurements) may not be needed. In some embodiments, ambient temperature monitoring may be performed for other functionality (e.g., measuring cabin temperature for pre-heating a vehicle, monitoring for high temperatures, etc.). In the decision step 310, if a person is present then the method 300 may move to the step 314.

In the step 314, the processor 134 may determine the characteristics of the people 70a-70d present within the interior 62. For example, the processor 134 may interpret the sensor readings from the radar device 130 to measure characteristics such as the heart rate, the breathing rate and/or the shapes detected and compare the readings to the stored data 182a-182c. Next, in the step 316, the ambient temperature sensor 132 may measure the ambient temperature of the interior 62 of the vehicle 60. For example, the ambient temperature sensor 132 may convert the measured temperature into an electrical signal and present the electrical signal T to the processor 134 (or the ECU 134'). In the step 318, the processor 134 may determine an urgency level based on the presence of the people 70a-70d, the characteristics of the people 70a-70d and/or the temperature measured. For example, the processor 134 may compare the sensor readings to the stored data 182a-182n (e.g., compared the measured readings to the stored statistical information). Next, the method 300 may move to the decision step 320.

In the decision step 320, the processor 134 may determine whether the urgency level indicates that one or more of the escalating responses should be performed. In an example, the processor 134 may compare the urgency level determined with the escalating response logic 182e. If the urgency level does not indicate one of the escalating responses should be performed, then the method 300 may return to the step 316. If the urgency level does indicate that one of the escalating responses should be performed, then the method 300 may move to the step 322. In the step 322, the processor 134 may generate one or more of the control signals EA-EN to perform one or more of the escalating responses based on the urgency level. In an example, the processor 134 (or the ECU 134') may be configured to activate one or more of the components 120a-120n. Next, the method 300 may return to the step 316.

Figure 7:
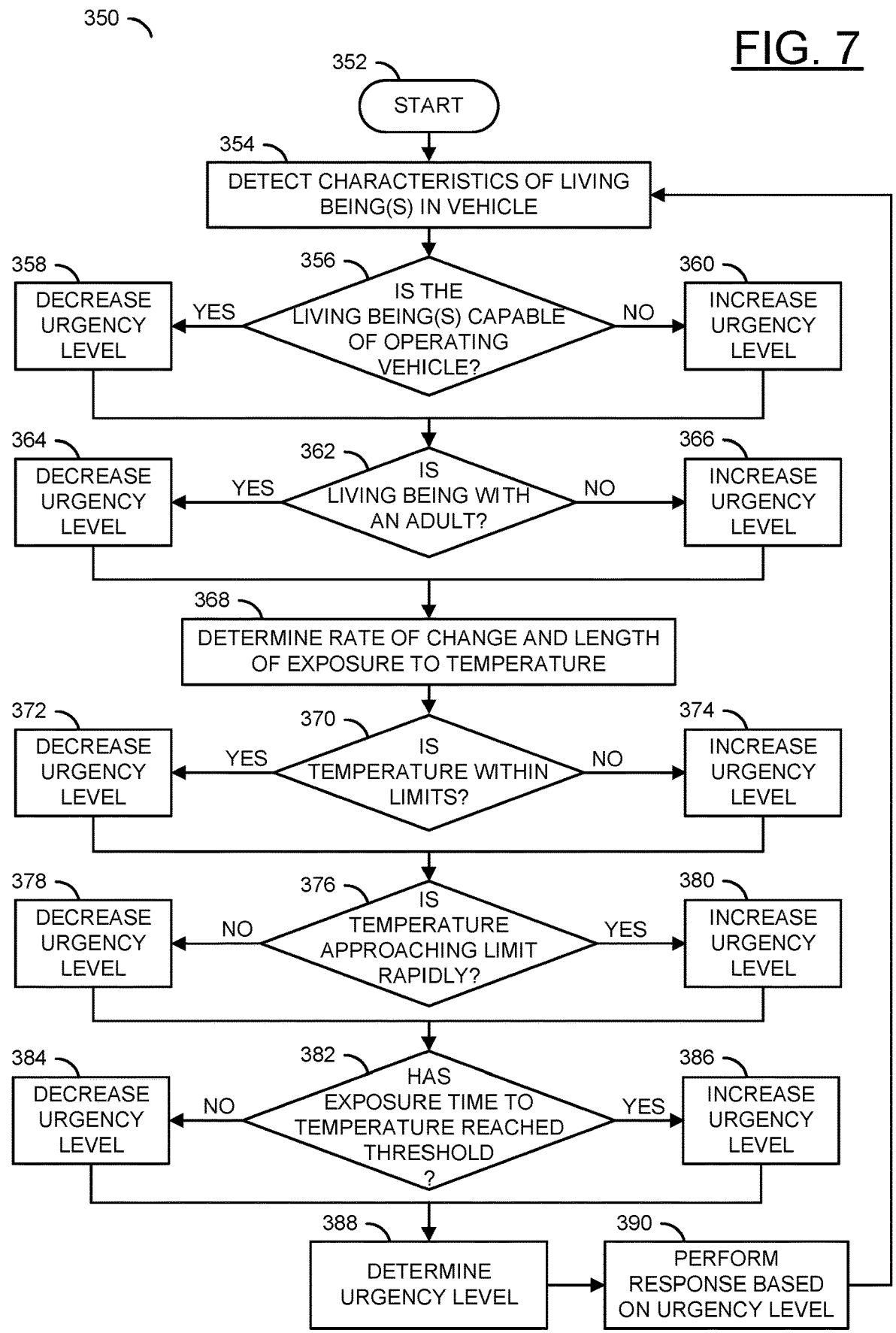
FIG. 7 is a flow diagram illustrating a method for adjusting an urgency level in response to sensor input.

Referring to FIG. 7, a method (or process) 350 is shown. The method 350 may adjust an urgency level in response to sensor input. The method 350 generally comprises a step (or state) 352, a step (or state) 354, a decision step (or state) 356, a step (or state) 358, a step (or state) 360, a decision step (or state) 362, a step (or state) 364, a step (or state) 366, a step (or state) 368, a decision step (or state) 370, a step (or state) 372, a step (or state) 374, a decision step (or state) 376, a step (or state) 378, a step (or state) 380, a decision step (or state) 382, a step (or state) 384, a step (or state) 386, a step (or state) 388, and a step (or state) 390.

The step 352 may start the method 350. In the step 354, the radar device 130 may perform measurements and the processor 134 may detect the characteristics of the living beings 70a-70d in the interior 62 of the vehicle 60. For example, the living beings 70a-70d may comprise children, adults, teenagers, the elderly, animals, etc. Next, the method 350 may move to the decision step 356.

In the decision step 356, the processor 134 may determine whether the living beings detected are capable of operating the vehicle 60. For example, an adult that is breathing normally and has a normal heart rate may be considered capable of controlling the various features of the vehicle (e.g., power on the vehicle, turn on heating/cooling, open the doors, etc.). In another example, children, pets and/or incapacitated people (e.g., based on the breathing rate and/or heart rate) may not be capable of controlling the various features of the vehicle. If a person that is capable of operating the vehicle 60 is detected, then the method 350 may move to the step 358. In the step 358, the processor 134 may decrease the urgency level. Next, the method 350 may move to the decision step 362. In the decision step 356, if a person that is capable of operating the vehicle 60 is not detected, then the method 350 may move to the step 360. In the step 360, the processor 134 may increase the urgency level. Next, the method 350 may move to the decision step 362.

In the decision step 362, the processor 134 may determine whether one of the living beings detected is an adult. For example, the ages of the detected people 70a-70d may be determined by comparing the breathing rates, heart rates and/or shapes of the detected people with the stored data 182a-182n. Generally, if a child (or an incapacitated person) is in the vehicle 60 with an able-bodied adult then the adult may be capable of operating the vehicle 60 (e.g., controlling the heating/cooling, removing the child, taking care of the incapacitated person, etc.). If at least one of the people is an adult that is capable of operating the vehicle 60, then the method 350 may move to the step 364. In the step 364, the processor 134 may decrease the urgency level. Next, the method 350 may move to the step 368. If a child (or other incapacitated person) is not with an adult that is capable of operating the vehicle 60, then the method 350 may move to the step 366. In the step 366, the processor 134 may increase the urgency level. Next, the method 350 may move to the step 368. In the step 368, the ambient temperature sensor 132 may measure the ambient temperature and the processor 134 may determine the rate of change of the temperature and/or a length of exposure of the living beings 70a-70d to the temperature conditions. For example, the processor 134 may track the temperature over time to determine how long the living beings 70a-70d have been exposed to particular temperature ranges. Next, the method 350 may move to the decision step 370.

In the decision step 370, the processor 134 may determine whether the measured temperature is within the acceptable limits. For example, the acceptable limits may be temperatures that are considered safe for people to be exposed to for long periods of time (e.g., a comfortable temperature, above freezing, below 32C/90F, etc.). If the measured temperature is within the acceptable limits, then the method 350 may move to the step 372. In the step 372, the processor 134 may decrease the urgency level. Next, the method 350 may move to the decision step 376. In the decision step 370, if measured temperature is outside of the acceptable limits, then the method 350 may move to the step 374. In the step 374, the processor 134 may increase the urgency level. Next, the method 350 may move to the decision step 376.

In the decision step 376, the processor 134 may determine whether the measured temperature is rapidly approaching the limits. For example, the processor 134 may measure the rate of change of the temperature. Even if the temperature is currently within the acceptable limits, the temperature may be quickly approaching (e.g., increasing or decreasing) temperatures that may not be safe. If the measured temperature is not rapidly approaching the acceptable limits, then the method 350 may move to the step 378. In the step 378, the processor 134 may decrease the urgency level. Next, the method 350 may move to the decision step 382. In the decision step 376, if measured temperature is rapidly approaching the acceptable limits, then the method 350 may move to the step 380. In the step 380, the processor 134 may increase the urgency level. Next, the method 350 may move to the decision step 382.

In the decision step 382, the processor 134 may determine whether an exposure time to the temperature has reached a predetermined threshold. For example, the processor 134 may measure how long the living beings 70a-70d have been exposed to particular temperature ranges. In an example, a person may be able to withstand some temperatures for a brief amount of time, but may not remain safe with continuing exposure. Similarly, different escalating responses may be performed based on how long the people have been exposed (e.g., rolling the windows down may help initially, but active cooling may need to be applied for continuing exposure). If the exposure time to a particular temperature has not reached the predetermined threshold, then the method 350 may move to the step 384. In the step 384, the processor 134 may decrease the urgency level. Next, the method 350 may move to the step 388. In the decision step 382, if the exposure time to a particular temperature has reached the predetermined threshold, then the method 350 may move to the step 386. In the step 386, the processor 134 may increase the urgency level. Next, the method 350 may move to the step 388.

In the step 388, the processor 134 may determine the urgency level. While a number of factors has been described as representative examples (e.g., people in the vehicle, temperature, exposure time, etc.) other factors may be considered for determining the urgency level. Next, in the step 390, the processor 134 may enable the response based on the urgency level (e.g., activate one or more of the components 120a-120n). Next, the method 350 may return to the step 354.

Figure 8:
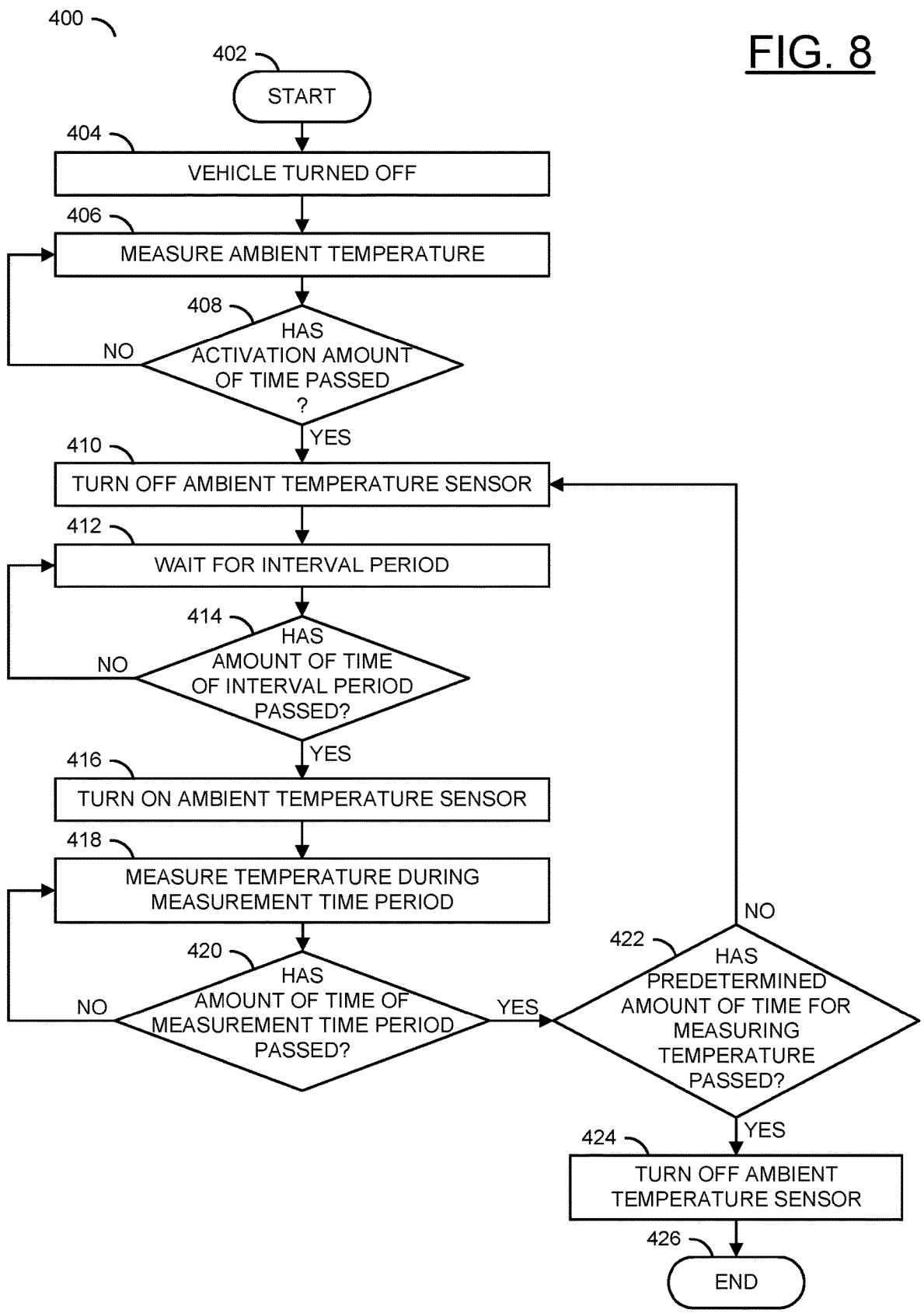
FIG. 8 is a flow diagram illustrating a method for periodically activating a radar unit after a vehicle has been turned off for power saving.

Referring to FIG. 8, a method (or process) 400 is shown. The method 400 may periodically activate a radar unit after a vehicle has been turned off for power saving. The method 400 generally comprises a step (or state) 402, a step (or state) 404, a step (or state) 406, a decision step (or state) 408, a step (or state) 410, a step (or state) 412, a decision step (or state) 414, a step (or state) 416, a step (or state) 418, a decision step (or state) 420, a decision step (or state) 422, a step (or state) 424, and a step (or state) 426.

The step 402 may start the method 400. In the step 404, the vehicle 60 may be turned off. Next, in the step 406, the ambient temperature sensor 132 may measure the ambient temperature of the interior 62. Next, the method 400 may move to the decision step 408.

In the decision step 408, the processor 134 (or the ECU 134') may determine whether an activation amount of time has passed. The activation amount of time may be a setting for how long the radar units 100a-100n remain on after the vehicle 60 has been powered off. If the activation amount of time has not passed, then the method 400 may return to the step 406 (e.g., the radar units 100a-100n may remain on and perform measurements). If the activation amount of time has passed, then the method 400 may move to the step 410. In the step 410, the processor 134 and/or the ECU 134' may turn off the ambient temperature sensor 132 (or the radar units 100a-100n may be powered off or operate in a low powered state). Next, in the step 412, the radar units 100a-100n may wait for an interval period. Next, the method 400 may move to the decision step 414.

In the decision step 414, the processor 134 (or the ECU 134' or another one of the powered on devices 104) may determine whether the interval period has passed. The interval period may be an amount of time that the radar units 100a-100n stay in a low powered mode of operation. The interval period may be a different amount of time than the activation amount of time. If the interval period has not passed, then the method 400 may return to the step 412 (e.g., remain in the low powered state). If the interval period has passed, then the method 400 may move to the step 416. In the step 416, the processor 134 (or the ECU 134' or another one of the powered on devices 104) may turn on the ambient temperature sensor 132 (or the radar units 100a-100n). Next, in the step 418, the ambient temperature sensor 132 may measure the temperature during the measurement time period. Next, the method 400 may move to the decision step 420.

In the decision step 420, the processor 134 (or the ECU 134' or another one of the powered on devices 104) may determine whether the measurement time period has passed. The measurement time period may be an amount of time that the radar units 100a-100n stay in a powered on (e.g., measuring) mode of operation. The measurement time period may be a different amount of time than the activation amount of time and/or the interval time period. If the amount of time of the measurement time period has not passed, then the method 400 may return to the step 418 (e.g., the radar units 100a-100n may continue performing measurements). If the amount of time of the measurement time period has passed, then the method 400 may move to the decision step 422.

In the decision step 422, the processor 134 (or the ECU 134' or another one of the powered on devices 104) may determine whether the predetermined amount of time for measuring temperature has passed. The predetermined amount of time for measuring temperature may be an amount of time that the radar units 100a-100n cycle between the powered on (e.g., measuring) mode of operation and the low powered mode of operation. The predetermined amount of time for measuring temperature may be a different amount of time than the activation amount of time, the interval time period and/or the measurement time period. In some embodiments, no amount of time for measuring temperature may be set (e.g., the radar units 100a-100n may continue cycling states the entire time the vehicle 60 is powered off). If the predetermined amount of time for measuring temperature has not passed, then the method 400 may return to the step 410 (e.g., return to the low powered state). If the predetermined amount of time for measuring temperature has passed, then the method 400 may move to the step 424. In the step 424, the processor 134 (or the ECU 134' or another one of the powered on devices 104) may turn off the ambient temperature sensor 132 (or the radar units 100a-100n). The ambient temperature sensor 132 (or the radar units 100a-100n) may remain off. Next, the method 400 may move to the step 426. The step 426 may end the method 400.

Referring to FIG. 9, a method (or process) 450 is shown. The method 450 may generate escalating actions in response to an urgency level. The method 450 generally comprises a step (or state) 452, a step (or state) 454, a step (or state) 456, a step (or state) 458, a decision step (or state) 460, a step (or state) 462, a step (or state) 464, a step (or state) 466, a decision step (or state) 468, a step (or state) 470, a decision step (or state) 472, a step (or state) 474, a decision step (or state) 476, a step (or state) 478, a step (or state) 480, and a step (or state) 482.

The step 452 may start the method 450. In the step 454, the processor 134 may activate the radar device 130 and the temperature sensor 132. Next, in the step 456, the processor 134 may determine the characteristics of the people 70a-70d in the interior 62 of the vehicle 60 from the readings performed by the radar device 130. In the step 458, the processor 134 may read the temperature from the readings performed by the ambient temperature sensor 132. Next, the method 450 may move to the decision step 460.

In the decision step 460, the processor 134 (or the ECU 134') may determine whether other temperature sensors in the vehicle 60 are active. For example, one or more of the powered on device 104 may comprise a temperature sensor. The processor 134 may receive temperature readings performed by other devices over the electronic bus 150. If other temperature sensors are active, then the method 450 may move to the step 462. In the step 462, the processor 134 may receive the temperature readings over the electronic bus 150 from the other sensors. Next, in the step 464, the processor 134 may calculate a weighted average of the temperatures and/or determine temperature differentials. For example, the processor 134 may perform a weighting on the calculated temperatures based on the recency of the data, the reliability of the measurements, a location of the sensors in the interior 62, etc. Next, the method 450 may move to the step 466. In the decision step 460, if no other temperature sensors are active, then the method 450 may move to the step 466. In the step 466, the processor 134 may determine the urgency level. For example, the processor 134 may compare the various sensor readings (e.g., characteristics, measured temperature, weighted temperature, etc.) and the escalating response logic 182e to determine how to respond to the current scenario. Next, the method 450 may move to the decision step 468.

In the decision step 468, the processor 134 may determine whether the urgency level is low. For example, the low urgency may correspond to a scenario where no urgent action is needed, but a warning may be appropriate (e.g., a child is in the car, but not currently in danger based on the temperature measured, the heart rate, the breathing rate, etc.). If the urgency level is low, then the method 450 may move to the step 470. In the step 470, the processor 134 may enable one or more of the components 120a-120n to generate a notification (e.g., the Wi-Fi device 120c may communicate a notification to a smartphone, send an email, send a text message, post a message to a social media account, etc.). For example, the alarm 80 may be suppressed by the escalating actions. Next, the method 450 may return to the step 456 (e.g., continue monitoring). In the decision step 468, if the urgency level is not low, then the method 450 may move to the decision step 472.

In the decision step 472, the processor 134 may determine whether the urgency level is medium. For example, the medium urgency may correspond to a scenario where no urgent action is needed, but danger may be imminent (e.g., a child is in the car, and the temperature is rapidly approaching the acceptable limits). If the urgency level is medium, then the method 450 may move to the step 474. In the step 474, the processor 134 may enable one or more of the components 120a-120n to generate the alarm sound 80 (e.g., the alarm 120a may generate a loud noise to alert people nearby). Next, the method 450 may return to the step 456 (e.g., continue monitoring). In the decision step 472, if the urgency level is not medium, then the method 450 may move to the decision step 476.

In the decision step 476, the processor 134 may determine whether the urgency level is high. For example, the high urgency may correspond to a scenario where urgent action is needed (e.g., a child is in the car, and the temperature is beyond the acceptable limits). If the urgency level is not high, then the method 450 may move to the step 478. In the step 478, the processor 134 may not perform one of the escalating responses (e.g., the people 70a-70d in the vehicle 60 may be comfortable). Next, the method 450 may return to the step 456 (e.g., continue monitoring). In the decision step 476, if the urgency level is high, then the method 450 may move to the step 480.

In the step 480, the processor 134 may enable one or more of the components 120a-120n to perform an intervention. In an example, one or more actuators may be powered to perform the intervention (e.g., turn on the HVAC 110a to adjust the temperature, open the windows, unlock/open the doors, etc.). In the method 450, three urgency levels are described as a representative example. A higher granularity of urgency levels may be implemented. The urgency levels may implement fuzzy logic. Which level of urgency corresponds to particular escalating responses may be varied according to the design criteria of a particular implementation. Next, the method 450 may move to the step 482. The step 482 may end the method 450.

The functions performed by the diagrams of FIGS. 1-9 may be implemented using one or more of a conventional general purpose processor, digital computer, microprocessor, microcontroller, RISC (reduced instruction set computer) processor, CISC (complex instruction set computer) processor, SIMD (single instruction multiple data) processor, signal processor, central processing unit (CPU), arithmetic logic unit (ALU), video digital signal processor (VDSP) and/or similar computational machines, programmed according to the teachings of the specification, as will be apparent to those skilled in the relevant art(s). Appropriate software, firmware, coding, routines, instructions, opcodes, microcode, and/or program modules may readily be prepared by skilled programmers based on the teachings of the disclosure, as will also be apparent to those skilled in the relevant art(s). The software is generally executed from a medium or several media by one or more of the processors of the machine implementation.

The invention may also be implemented by the preparation of ASICs (application specific integrated circuits), Platform ASICs, FPGAs (field programmable gate arrays), PLDs (programmable logic devices), CPLDs (complex programmable logic devices), sea-of-gates, RFICs (radio frequency integrated circuits), ASSPs (application specific standard products), one or more monolithic integrated circuits, one or more chips or die arranged as flip-chip modules and/or multi-chip modules or by interconnecting an appropriate network of conventional component circuits, as is described herein, modifications of which will be readily apparent to those skilled in the art(s).

The invention thus may also include a computer product which may be a storage medium or media and/or a transmission medium or media including instructions which may be used to program a machine to perform one or more processes or methods in accordance with the invention. Execution of instructions contained in the computer product by the machine, along with operations of surrounding circuitry, may transform input data into one or more files on the storage medium and/or one or more output signals representative of a physical object or substance, such as an audio and/or visual depiction. The storage medium may include, but is not limited to, any type of disk including floppy disk, hard drive, magnetic disk, optical disk, CD-ROM, DVD and magneto-optical disks and circuits such as ROMs (read-only memories), RAMS (random access memories), EPROMs (erasable programmable ROMs), EEPROMs (electrically erasable programmable ROMs), UVPROMs (ultra-violet erasable programmable ROMs), Flash memory, magnetic cards, optical cards, and/or any type of media suitable for storing electronic instructions.

The elements of the invention may form part or all of one or more devices, units, components, systems, machines and/or apparatuses. The devices may include, but are not limited to, servers, workstations, storage array controllers, storage systems, personal computers, laptop computers, notebook computers, palm computers, cloud servers, personal digital assistants, portable electronic devices, battery powered devices, set-top boxes, encoders, decoders, transcoders, compressors, decompressors, pre-processors, post-processors, transmitters, receivers, transceivers, cipher circuits, cellular telephones, digital cameras, positioning and/or navigation systems, medical equipment, heads-up displays, wireless devices, audio recording, audio storage and/or audio playback devices, video recording, video storage and/or video playback devices, game platforms, peripherals and/or multi-chip modules. Those skilled in the relevant art(s) would understand that the elements of the invention may be implemented in other types of devices to meet the criteria of a particular application.

The terms "may" and "generally" when used herein in conjunction with "is(are)" and verbs are meant to communicate the intention that the description is exemplary and believed to be broad enough to encompass both the specific examples presented in the disclosure as well as alternative examples that could be derived based on the disclosure. The terms "may" and "generally" as used herein should not be construed to necessarily imply the desirability or possibility of omitting a corresponding element.

The designations of various components, modules and/or circuits as "a"-"n", when used herein, disclose either a singular component, module and/or circuit or a plurality of such components, modules and/or circuits, with the "n" designation applied to mean any particular integer number. Different components, modules and/or circuits that each have instances (or occurrences) with designations of "a"-"n" may indicate that the different components, modules and/or circuits may have a matching number of instances or a different number of instances. The instance designated "a" may represent a first of a plurality of instances and the instance "n" may refer to a last of a plurality of instances, while not implying a particular number of instances.

While the invention has been particularly shown and described with reference to embodiments thereof, it will be understood by those skilled in the art that various changes in form and details may be made without departing from the scope of the invention.

The invention claimed is:

1. An apparatus comprising:
   a radar component configured to (i) detect a presence of a person in a vehicle and (ii) determine an age range of said person detected; and
   a temperature sensor configured to determine an ambient temperature in said vehicle, wherein
   (a) said apparatus is configured to operate when said vehicle is turned off,
   (b) a processor is configured to determine an urgency level in response to (i) said age range of said person detected and (ii) said ambient temperature,
   (c) said processor is configured to generate escalating actions in response to said urgency level, and
   (d) said urgency level comprises (i) a first level when said age range of said person corresponds to a child and said ambient temperature is (1) below an upper threshold and increasing at a low rate or (2) above a lower threshold and decreasing at said low rate, (ii) a second level when said age range of said person corresponds to said child and said ambient temperature is (1) below said upper threshold and increasing at a high rate or (2) above said lower threshold and decreasing at said high rate, and (iii) a third level when said age range of said person corresponds to said child and said ambient temperature is (1) above said upper threshold or (2) below said lower threshold.

2. The apparatus according to claim 1, wherein said temperature sensor is configured to measure said ambient temperature continually for a predetermined amount of time after said vehicle is turned off.

3. The apparatus according to claim 1, wherein said apparatus is further configured to (i) enable said temperature sensor to measure said ambient temperature continuously for an activation amount of time after said vehicle is turned off, (ii) turn off after said activation amount of time, (iii) turn on after an interval time period to enable said temperature sensor to measure said ambient temperature, (iv) turn off after a measurement time period and (v) repeat (iii)-(iv) for a predetermined amount of time while said vehicle is turned off.

4. The apparatus according to claim 1, wherein said escalating actions comprise (i) a warning when said urgency level is at said first level, (ii) an alert when said urgency level is at said second level and (iii) generating a signal to perform an intervention when said urgency level is at said third level.

5. The apparatus according to claim 4, wherein said signal is configured to open a window of said vehicle.

6. The apparatus according to claim 4, wherein said signal is configured to activate a heating and cooling system of said vehicle.

7. The apparatus according to claim 1, wherein said urgency level is increased based on said ambient temperature regardless of said age range of said person.

8. The apparatus according to claim 1, wherein said person comprises at least one of an elderly person, a differently-abled person, said child, and an animal.

9. The apparatus according to claim 1, wherein (i) said apparatus is further configured to receive temperature information from a component of said vehicle, (ii) perform a weighted average of said ambient temperature and said temperature information and (iii) adjust said urgency level in response to said weighted average.

10. The apparatus according to claim 1, wherein said radar component is configured to determine said age range of said person detected in response to (a) measuring a breathing rate of said person detected and (b) comparing said breathing rate measured to known breathing rates for said age range.

11. The apparatus according to claim 1, wherein said radar component is further configured to (i) determine whether a second person is detected in said vehicle and (ii) adjust said urgency level if said age range of said second person corresponds to an adult.

12. The apparatus according to claim 1, wherein said apparatus is configured to be operational (i) while said vehicle is off and (ii) while a heating and cooling system of said vehicle is powered off.

13. The apparatus according to claim 1, wherein said processor is a component of said apparatus.

14. The apparatus according to claim 1, wherein (i) said processor is a component of an electronic control unit, (ii) said radar component is configured to present said presence detected as a first input to said electronic control unit and (iii) said temperature sensor is configured to present said ambient temperature as a second input to said electronic control unit.

15. The apparatus according to claim 1, wherein (i) said apparatus is configured to generate an alarm in response to said presence of said child detected in said vehicle when said vehicle is turned off and (ii) said escalating actions are configured to suppress said alarm based on said urgency level.

16. The apparatus according to claim 1, wherein said urgency level is adjusted based on whether an exposure time of said person to said ambient temperature has reached a predetermined threshold.

17. An apparatus comprising:
 a radar component configured to (i) detect a presence of a person in a vehicle and (ii) determine an age range of said person detected; and
 a temperature sensor configured to determine an ambient temperature in said vehicle, wherein
  (a) said apparatus is configured to operate when said vehicle is turned off,
  (b) a processor is configured to determine an urgency level in response to (i) said age range of said person detected and (ii) said ambient temperature,
  (c) said processor is configured to generate escalating actions in response to said urgency level, and
  (d) said urgency level comprises (i) a first level when ambient temperature is above a lower threshold and decreasing at a low rate, (ii) a second level when said ambient temperature is above said lower threshold and decreasing at a high rate and (iii) a third level when said ambient temperature is below said lower threshold.

18. The apparatus according to claim 17, wherein said radar component is configured to determine said age range of said person detected in response to (a) measuring a heart beat rate and a shape of said person detected and (b) comparing said heart beat rate and said shape measured to known heart beat rates for said age range.

19. An apparatus comprising:
 a radar component configured to (i) detect a presence of a person in a vehicle and (ii) determine an age range of said person detected; and
 a temperature sensor configured to determine an ambient temperature in said vehicle, wherein
  (a) said apparatus is configured to operate when said vehicle is turned off,
  (b) a processor is configured to determine an urgency level in response to (i) said age range of said person detected and (ii) said ambient temperature,
  (c) said processor is configured to generate escalating actions in response to said urgency level, and
  (d) said urgency level comprises (i) a first level when said ambient temperature is below an upper threshold and increasing at a low rate, (ii) a second level when said ambient temperature is below said upper threshold and increasing at a high rate and (iii) a third level when said ambient temperature is above said upper threshold.

20. The apparatus according to claim 19, wherein said temperature sensor is configured to measure said ambient temperature continually for a predetermined amount of time after said vehicle is turned off.

* * * * *